(12) United States Patent
Changeux et al.

(10) Patent No.: US 6,177,242 B1
(45) Date of Patent: Jan. 23, 2001

(54) GENOMIC DNA FRAGMENTS CONTAINING REGULATORY AND CODING SEQUENCES FOR THE β2-SUBUNIT OF THE NEURONAL NICOTINIC ACETYLCHOLINE RECEPTOR AND TRANSGENIC ANIMALS MADE USING THESE FRAGMENTS OR MUTATED FRAGMENTS

(75) Inventors: Jean-Pierre Changeux; Marina Picciotto; Alain Bessis, all of Paris (FR)

(73) Assignee: Institut Pasteur, Paris (FR)

( * ) Notice: Under 35 U.S.C. 154(b), the term of this patent shall be extended for 0 days.

(21) Appl. No.: 08/358,627

(22) Filed: Dec. 14, 1994

(51) Int. Cl.[7] ............... C12Q 1/68; C12N 15/00; C12N 5/00; C07H 21/04
(52) U.S. Cl. ............ 435/6; 435/320.1; 435/325; 435/235.1; 530/350; 536/24.1; 536/23.1; 536/23.5
(58) Field of Search .................. 536/23.1, 23.5, 536/24.1; 435/325, 320.1, 235.1, 172.3, 4, 6.1, 7.1; 530/350

(56) References Cited

FOREIGN PATENT DOCUMENTS

WO 91/15602 * 10/1991 (WO) .

OTHER PUBLICATIONS

Molecular Cloning. Sambrook et al., pp. 2.11–2.15, 1989.*

* cited by examiner

*Primary Examiner*—Deborah J. Clark
(74) *Attorney, Agent, or Firm*—Finnegan, Henderson, Farabow, Garrett & Dunner, L.L.P.

(57) ABSTRACT

Several genes encoding subunits of the neuronal nicotinic acetylcholine receptors have been cloned and regulatory elements involved in the transcription of the α:2 and α:7-subunit genes have been described. Yet, the detailed mechanisms governing the neuron-specific transcription and the spatio-temporal expression pattern of these genes remain largely uninvestigated. The β2-subunit is the most widely expressed neuronal nicotinic receptors subunit in the nervous system. We have studied the structural and regulatory properties of the 5' sequence of this gene. A fragment of 1163 bp of upstream sequence is sufficient to drive the cell-specific transcription of a reporter gene in both transient transfection assays and in transgenic mice. Deletion analysis and site-directed mutagenesis of this promoter reveal two negative and one positive element. The positively acting sequence includes one functional E-box. One of the repressor elements is located in the transcribed region and is the NRSE/RE1 sequence already described in promoters of neuronal genes.

42 Claims, 15 Drawing Sheets

-1125 GGAATTCCTG AAAACACTCA AGTTTAAGTA AAAGGTAGGT AGGGGCACTG GGG<u>TGATAAA</u>
       *EcoRI*                                                    *GATA-3*

-1065 AGAGCTGGAG GGAACTACAT GTTTAAAAGA CCGAGGGCTA GGAGGGGTTA AATAGTCAAG
                                            1006E|→
-1005 GATCTTAAAG ACGTCGTCAA TAGCTAGAAT GTGGAGCTGA GACAGGCATT GACGAGATGA

-945  AGTCCGAAGC CTTTTGTCTG CTAAGTCTGC TTCAGACAGA AATCTTTTTG GTTGAAAGTG

-885  ACCACTGATC CACTAAGAAA AAAAAGAGG TCCTTTTTGG GCTCAGTAGC TAAAACGGCA
             |→862E
-825  GGGCTTTCAA GATCAAACAT GTCATTGAGT TTTGACACCT CTCTCATCTT TGCTCTCTTT

-765  GTGTTAGCTT CATTCTTTCT GTGAAATGGT CCCCTGATCT CCCCAGAACA CAGCGTGGAA

-705  GGAACCATTG ATATTGGTTG CTTATGCAGA TCTCAGAACT TTCAAGGCCA CCTTCTTTTC

-645  AGGAGGTCTA GACCTATCTA GCTTAGATTC CCCAGGAGAA TGGCAAGATC TTGGCCTTGT

-585  CTGAGCTTAT GGAAGCAGAG AAGGGGGCAG GTGCAAAAGA CTCTCTTCCA GAACTCCGGA

-525  GAAATTTGCT TTTCAAAACT AGACAGCACC CTGCTGCCTA CTAAAGAAGT AGGTCCAAGG

-465  TCCTAATGTG CATATTCTCC GCTATACTCT TAGCTTTCCA GAAAACTAGA ATCATCAGTT

-405  TGGGTAAGAA CATAGAGGAA AACAGAAACG CCCCCCAACC TACCCCATGT CCAGAGAGCC

-345  TTGACCTACT TGTCTCCCTC CCACTCTCAA CCCTCCCAGT CTTGCTTCAA ACCTCTCC<u>AC</u>
                                                        283E|→
-285  <u>GTCATGCCCC</u> AACTTCGGAG CATTTGAACT CTGAGCAGTG GGGTCGCTTT CGCCTCAAGC
      *CREB*

-225  ACACCCCACC TCGGCAGGCC CAGTCAAAGG TCCCTCACAG GACACCTTT TTTTCCCTGG

-165  GATCCCGCGC TTCGCCTCCG <u>GGGCGG</u>AGAC TCCTCCCCTA GTAGTTC<u>C</u>AC TT<u>G</u>TGTTCCC
                           *SP1*                                *E-Box*

↓r    133E|→           ↓h
-105  TAGAAGAGCA GCCGGGACGG CAAGAAGCCG GGACCTCCCC CTTCGTTCCA GGAACTGCCG
                                                ▽      ▽       ▽       ▽
-45   CGCAGTGGGC ACTTCAGCCC TGGAGGCCGC GAGCCCCACC CGGGT<u>G</u>AAGG CGGCTGCGCG
                                                        +1
+16   GC<u>TTCAGCAC CACGGACAGC GC</u>TCCCGTCC GCAGCCCTTG TGTCAGCGAG CGTCCGCGCT
           *NRSE/RE1*   *Eco47III*

+76   CGCGCTATGC AGGCGC<u>ATGG</u> CCCGGTGCTC AACTCTATG GCGCTGCTGT TCAGCTTTGG

+136  CCTCCTTTGG CTGTGTTCAG gtaagaatt (SEQ ID NO:22)

FIG. 1

| NUCLEUS | GENOTYPE | # CELLS TESTED | RESPONSES | % RESPONSE |
|---|---|---|---|---|
| ANTERO-DORSAL THALAMUS | +/+ | 22 | 22 | 100 |
| | -/- | 15 | 0 | 0 |
| LATERO-DORSAL THALAMUS | +/+ | 14 | 14 | 100 |
| | -/- | 9 | 0 | 0 |
| ANTERO-VENTRAL THALAMUS | +/+ | 36 | 36 | 100 |
| | -/- | 10 | 0 | 0 |
| MEDIAL HABENULA | +/+ | 8 | 8 | 100 |
| | -/- | 9 | 8 | 89 |

FIG. 10B

GENOMIC DNA FRAGMENTS CONTAINING REGULATORY AND CODING SEQUENCES FOR THE β2-SUBUNIT OF THE NEURONAL NICOTINIC ACETYLCHOLINE RECEPTOR AND TRANSGENIC ANIMALS MADE USING THESE FRAGMENTS OR MUTATED FRAGMENTS

BACKGROUND OF THE INVENTION

Field of the Invention

This invention relates to DNA and clones of β2-subunit of neuronal nicotinic acetylcholine receptor (nAChR) sequences. This invention also relates to genomic DNA fragments containing regulatory and coding sequences for the β2-subunit neuronal nAChR and transgenic animals made using these fragments or mutated fragments. The 5' flanking sequences contain a promoter, which confers neuron-specific expression. The genomic clones demonstrate the importance of the β2-subunit gene in the nicotinic system and in the pharmacological response to nicotine. The invention also relates to vectors containing the DNA sequences, cells transformed with the vectors, transgenic animals carrying the sequences, and cell lines derived from these transgenic animals. In addition, the invention describes the uses of all of the above.

References cited in this specification appear at the end by author and publication year or by cite number.

Neuron-specific expression. Many recombinant DNA-based procedures require tissue-specific expression. Unwanted or potentially harmful side-effects of gene transfer therapies and procedures can be reduced through correct tissue-specific expression. Furthermore, the ability to direct the expression of certain proteins to one cell type alone advances the ability of scientists to map, identify or purify these cells for important therapeutic or analytical purposes. Where the cells of interest are neurons or a particular subset of neurons, a need for DNA sequences conferring neuron-specific or subset-specific expression exists.

Proteins expressed throughout an organism are often utilized for specific purposes by neurons. By expressing a particular subunit or component of these proteins solely in neuronal tissue, the neuron tailors the protein activity for its purposes. Finding the particular, neuron-specific subunits or components and unraveling why they are produced only in neuronal tissue holds the key to DNA elements conferring neuron-specific expression. The inventors' knowledge of the biology of acetylcholine receptors provided an important foundation for this invention (see Changeux, The New Biologist, vol. 3, no.5, pp. 413–429). Different types of acetylcholine receptors are found in different tissues and respond to different agonists. One type, the nicotinic acetylcholine receptor (nAChR), responds to nicotine. A subgroup of that type is found only in neurons and is called the neuronal nAChR.

Generally, five subunits make up an acetylcholine receptor complex. The type of subunits in the receptor determines the specificity to agonists. It is the expression pattern of these subunits that controls the localization of particular acetylcholine receptor types to certain cell groups. The genetic mechanisms involved in the acquisition of these specific expression patterns could lead to an ability to control tissue-specific or even a more defined cell group-specific expression. The inventors' work indicates that defined elements in the promoter sequence confer neuron specific expression for the β2-subunit.

The Pharmacological Effects of Nicotine. As noted above, nAChR responds to the agonist nicotine. Nicotine has been implicated in many aspects of behavior including learning and memory (1,2). The pharmacological and behavioral effects of nicotine involve the neuronal nAChRs. Studies using low doses of nicotine (23) or nicotinic agonists (16) suggest that high affinity nAChRs in the brain mediate the effects of nicotine on passive avoidance behavior. Model systems where neuronal nAChR has been altered can therefore provide useful information on the pharmacological effects of nicotine, the role of neuronal nAChR in cognitive processes, nicotine addiction, and dementias involving deficits in the nicotinic system.

Functional neuronal nAChRs are pentameric protein complexes containing at least one type of α-subunit and one type of β-subunit (3–5) (although the α7-subunit can form functional homooligomers in vitro[6,7]). The β2-subunit was selected for this study from among the 7 known α-subunits and 3 known β-subunits (3) because of its wide expression in the brain (8–10), and the absence of expression of other β-subunits in most brain regions (10). Mutation of this subunit should therefore result in significant deficits in the CNS nicotinic system. The inventors have examined the involvement of the β2-subunit in pharmacology and behavior. Gene targeting was used to mutate the β2-subunit in transgenic mice.

The inventors found that high affinity binding sites for nicotine are absent from the brains of mice homozygous for the β2-subunit mutation, β2−/−. Further, electrophysiological recording from brain slices reveals that thalamic neurons from these mice do not respond to nicotine application. Finally, behavioral tests demonstrate that nicotine no longer augments the performance of β2−/−mice on the test of passive avoidance, a measure of associative learning. Paradoxically, mutant mice are able to perform better than their non-mutant siblings on this task.

BRIEF SUMMARY OF THE INVENTION AND ITS UTILITY

In an aspect of this invention, we describe a 15 kb fragment of DNA carrying regulatory and coding regions for the β2-subunit of the neuronal nAchR. We characterize the promoter of the β2-subunit gene in vitro and in transgenic mice. We describe several DNA elements, including an E-box and other consensus protein-binding sequences involved in the positive regulation of this gene. Moreover, we show that the cell-specific transcription of the β2-subunit promoter involves at least two negative regulatory elements including one located in the transcribed sequence.

Preferred embodiments of these aspects relate to specific promoter sequences and their use in directing neuron-specific expression in various cells and organisms. An 1163 bp sequence and an 862 bp sequence both confer neuron-specific expression. Other embodiments include the −245 to −95 sequence of FIG. 1, containing an essential activator element, and the −245 to −824 sequence of FIG. 1 containing a repressor. A repressor element composed of the NRSE/RE1 sequence is also present in the transcribed region. Certain plasmids comprising these genomic sequences are described as well.

The promoter sequences are important for their ability to direct protein, polypeptide or peptide expression in certain defined cells. For example, in the transgenic mice as shown below, proteins encoding toxins or the like can be directed to neurons to mimic the degradation of those cells in disease states. Others will be evident from the data described below.

Alternatively, the promoters can direct encoded growth factors or oncogenic, tumorigenic, or immortalizing proteins to certain neurons to mimic tumorigenesis. These cells can then be isolated and grown in culture. In another use, the promoter sequences can be operatively linked to reporter sequences in order to identify specific neurons in situ or isolate neurons through cell sorting techniques. The isolated, purified neurons can then be used for in vitro biochemical or genetic analysis. Reporter sequences such as LacZ and Luciferase are described below.

In another aspect of this invention, the inventors provide the genomic clones for mouse β-2 subunit of the neuronal nAChR. These clones are useful in the analysis of the mammalian nicotinic system and the pharmacology of nicotine. The inventors describe assays using transgenic mice where the genomic clones of the β2-subunit have been used to knock out the high affinity binding of nicotine.

In addition to the deletion mutants described, mutations incorporated into the exons or regulatory sequences for the β2-subunit will result in useful mutant transgenic animals. These mutations can be point mutations, deletions or insertions that result in non-efficient activity of the nAChR or even a non-active receptor. With such mutant animals, methods for determining the ability of a compound to restore or modulate the nAChR activity or function are possible and can be devised. Modulation of function can be provided by either up-regulating or down-regulating receptor number, activity, or other compensating mechanisms. Also, methods to determine the ability of a compound to restore or modulate wild type behavior in the behavioral assays described or known (see 17, 22, 18, 2, 19, 21, 23, 24) can be devised with the mutant animals. Behavioral assays comprise, but are not limited to, testing of memory, learning, anxiety, locomotor activity, and attention as compared to the untreated animal or patient. Pharmacological assays (see 12, 13, 14, 15, 20) to select compounds that restore or modulate nAChR-related activity or behavior can thus be performed with the mutant animals provided by this invention. Dose and quantity of possible therapeutic agents will be determined by well-established techniques. (See, for example, reference 16.)

The present model systems comprising transgenic animals or cells derived from these animals can be used to analyze the role of nicotine on learning and behavior, the pharmacology of nicotine, nicotine addiction, and disease states involving deficits in the nicotinic system. In addition, potential therapies for nicotine addiction or deficits in the nicotinic system can be tested with the transgenic animals or the cells and cell lines derived from them or any cell line transfected with a DNA fragment or the complete DNA of phage β2 (CNCM accession number I-1503). These cell lines would include all those obtained directly from homozygous or heterozygous transgenic animals that carry or are mutated in the β2-subunit sequences. In addition, this would include cell lines created in culture using natural β2-subunit sequences or mutated β2-subunit sequences. Techniques used could be, for example, those cited in PCT WO 90/11354.

Dementias, such as Alzheimer's disease, in which the high affinity nicotine binding site are diminished suggest that the present model can be used to screen drugs for compensation of this deficit. Accordingly, methods for screening compounds for the ability to restore or detectably effect activity of the neuronal nicotinic acetylcholine receptor comprising adding the compound to an appropriate cell line or introducing the compound into a transgenic animal can be devised. Transgenic animals and cell lines generated from this invention can be used in these methods. Such animal or cell line systems can also be used to select compounds which could be able to restore or to modulate the activity of the β2 gene.

The transgenic animals obtained with the β2-subunit gene sequence (wildtype or mutated fragments thereof) can be used to generate double transgenic animals. For this purpose the β2-subunit transgenic animal can be mated with other transgenic animals of the same species or with naturally occurring mutant animals of the same species. The resulting double transgenic animal, or cells derived from it, can be used in the same applications as the parent β2-subunit transgenic animal.

Both the promoter sequences and the genomic clones can be used to assay for the presence or absence of regulator proteins. The gel shift assays below exemplify such a use. The sequences or clones can also be used as probes by incorporating or linking markers such as radionuclides, fluorescent compounds, or cross-linking proteins or compounds such as avidin-biotin. These probes can be used to identify or assay proteins, nucleic acids or other compounds involved in neuron action or the acetylcholine receptor system.

Known methods to mutate or modify nucleic acid sequences can be used in conjunction with this invention to generate useful β2 mutant animals, cell lines, or sequences. Such methods include, but are not limited to, point mutations, site-directed mutagenesis, deletion mutations, insertion mutations, mutations obtainable from homologous recombination, and mutations obtainable from chemical or radiation treatment of DNA or cells bearing the DNA. DNA sequencing is used to determine the mutation generated if desired or necessary. The mutant animals, cell lines or sequences are then used in the DNA sequences, systems, assays, methods or processes the inventors describe. The mutated DNA will, by definition, be different, or not identical to the genomic DNA. Mutant animals are also created by mating a first transgenic animal containing the sequences described here or made available by this invention, with a second animal. The second animal can contain DNA that differs from the DNA contained in the first animal. In such a way, various lines of mutant animals can be created.

Furthermore, recombinant DNA techniques are available to mutate the DNA sequences described here, as above, link these DNA sequences to expression vectors, and express the β2-subunit protein or mutant derived from the β2-subunit sequences. The β2-subunit or mutant can thus be analyzed for biochemical or behavioral activity. In such a way, mutated DNA sequences can be generated that prevent the expression of an efficient nAchR.

Alternatively, the promoter sequences described can be used in expression vectors or systems to drive expression of other proteins. Obtainable DNA sequence can thus be linked to the promoter or regulatory sequences the inventors describe in order to transcribe those DNA sequences or produce protein, polypeptide, or peptides encoded by those DNA sequences.

DESCRIPTION OF THE RELATED ART

Previous studies by in situ hybridization (Wada et al., 1989; Hill et al., 1993; Zoli et al., 1994) and immunohistochemistry (Hill et al., 1993) demonstrate that all of the neuronal nAchR subunits cloned to date display a strict neuron-specific distribution. But different subunits exhibit an even tighter distribution to only small subsets of neurons in the brain. For example, the nAchR α2-subunit transcripts are only detected in the *Spiriformis lateralis* nucleus in the chick diencephalon (Daubas et al., 1990) or the Interpeduncularis nucleus in the rat (Wada et al., 1988). Also the β3, β4 and α3-subunit transcripts are only detected in a small set of structures in vertebrate brain (references in Zoli et al., 1994).

The nAchR, α4, α5, α7, and β2-subunit gene transcripts, in comparison, show a much wider distribution. (Wada et al., 1989; references in Zoli et al., 1994). For example, the β2-subunit transcripts are found in the majority of neurons in the CNS and in all the peripheral neurons that express the nAchR (Role, 1992; Hill et al., 1993).

As a consequence of the differential expression of these subunits, a wide diversity of nAchR species occurs in vertebrates. Each species has a defined pattern of expression involving diverse categories or groups of neurons. For example, the neurons from medial Habenula interconnect with those from the Interpeduncularis nucleus and yet each express distinct sets of nAchR subunits (see Role, 1992 for review) exhibiting different physiological and pharmacological profiles (Mulle et al., 1991).

Only limited information is available, to date, about the genetic mechanisms that account for regulation of nAchR gene transcription in neurons. Previous work on the promoter of the chick α7 subunit gene analyzed in vitro failed to characterize the DNA elements responsible for transcriptional regulation (Matter-Sadzinski et al., 1992). In another study, the promoter of the α2-subunit gene was partially characterized and a silencer described and sequenced (Bessis et al., 1993, see also Daubas et al. 1993).

Certain evidence leads to the study of the β2-subunit in particular. It is expressed in the majority of the neurons in the brain (Hill et al., 1993). Also, the timing of the appearance of the β2-transcripts closely parallels that of neuronal differentiation (Zoli et al., 1994). We thus decided to study the genetic mechanisms that regulate its transcription.

BRIEF DESCRIPTION OF THE INVENTION

Gene Structure

We have cloned a genomic fragment containing the regulatory sequences and sequences encoding the mouse nAchR β2-subunit gene. The inventors have found that at least part of the regulatory region is conserved among different mammalian species. Particularly, the region between +16 to +38 bp corresponding to the NRSE/RE1 as described in FIG. 1. Using RNase protection and amplification of primer extension products, we found one main and three minor transcription start sites (FIG. 1). The primer extension experiments were performed using two different reverse transcriptases, with different batches of mRNA and with different primers. These PCR based techniques allowed us to amplify and subclone the same fragments corresponding to transcription start sites rather than reverse transcriptase stops. The transcription start sites that we have characterized are located downstream from the position of the longest rat (Deneris et al., 1988) and human (Anand and Lindstrom, 1990) β2 cDNA 5' end (see FIG. 1). This implies that in human and rat, another transcription start site is used. Such a discrepancy between species has already been demonstrated for the ε-subunit of the muscle nAchR (Dürr et al., 1994, see also Dong et al., 1993; Toussaint et al., 1994). In contrast with the α2 subunit gene (Bessis et al., 1993), no upstream exon could be detected.

Structural analysis of a 1.2 kbp flanking region disclosed many consensus motifs for nuclear protein binding including an SpI site and an E-box. Approximately 90 bp of the undeleted 1.2 kb promoter are transcribed and this region contains a NRSE/RE1 sequence (Kraner et al., 1992; Mori et al., 1992). Regulatory elements have already been described downstream of the transcription start site in different systems such as the Polyomavirus (Bourachot et al., 1989) or the fos gene (Lamb et al., 1990).

The promoter region is located between the Eco47III located in exon 1 (see FIG. 1) (SEQ ID NO:22) and the BamHI site 4.5 kb upstream. One preferred embodiment is the 1163 bp sequence described in FIG. 1 between the EcoRI and Eco47III sites. Regulatory sequences may be located in the 2 kb downstream from the Eco47III site. The regulatory elements from the nAchR β2-subunit sequences can be used to direct the neuron specific expression of a nucleotide sequence encoding a protein, polypeptide or peptide linked to them. Said protein, polypeptide, or peptide can be toxins, trophic factors, neuropeptides, tumorigenic, oncogenic, or immortalizing proteins, or any other protein that can change the function of the neuron.

A 1163 bp, Promoter Achieves Cell-Specific Transcription

The 1163 bp promoter contains regulatory sequences for both tissue-specific and temporal specific transcription of the β2-subunit gene. Transient transfection experiments showed that the 1163 bp fragment contains sufficient information to confer cell-specific expression of the nAchR β2-subunit gene. We showed that the same promoter directs a strict cell-specific transcription of the β-galactosidase (β-gal) reporter gene. Moreover, the transgenic construct appears to be activated with the same timing as the endogenous β2-subunit gene during the development of the early embryonic nervous system (Zoli et al., 1994). At later stages of development, most of the peripheral β2 expressing neurons are still labelled (FIGS. 4C, D).

The promoter sequence was tested in transgenic mice by generating two lines (13 and 26) expressing β-gal under the control of the β2-subunit promoter. In CNS, the pattern of β-galactosidase expression is different between the two lines. Only a subset of the cells that normally express β2 express the transgene. This type of discrepancy between the expression of the transgene and the endogenous gene has already been described for the dopamine β-hydroxylase gene promoter (Mercer et al., 1991; Hoyle et al., 1994) or for the GAP-43 gene (Vanselow et al., 1994). Unexpected expression has been observed in transgenic line 13 in the genital tubercule and in skin muscles. This expression is likely to be due to the integration site of the transgene as these tissues are not stained in line 26. To our knowledge, most of the neuronal promoters studied by transgenesis display ectopic expression in a certain small percentage of transgenic lines (Forss-Petter et al., 1990; Kaneda et al., 1991; Banerjee et al., 1992; Hoesche et al., 1993; Logan et al., 1993, Vanselow et al., 1994). However, techniques in the art afford the construction of lines where the expression pattern of the transgene closely mirrors or duplicates that of the original gene. See references for further details showing the success of the transgenesis procedure.

By comparing the β-gal positive cell distribution with those of other known neuronal markers, it becomes apparent that a similarity exists with the distribution of choline acetyltransferase, TrkA (the high affinity nerve growth factor receptor) and $p^{75}$ (the low affinity nerve growth factor receptor) expressing cells (Yan and Johnson, 1988: Pioro and Cuello, 1990a, b; Ringstedt et al., 1993). In particular, in developing rats, $p^{75}$ is expressed in almost all the peripheral ganglia and central nuclei (with the exception of the zona incerta and hypothalamic nuclei), which express the transgene (Yan and Johnson, 1988). It is also interesting to note that p[75] expression (like the expression of the β2-promoter transgene) is transient in many peripheral ganglia and brain nuclei, decreasing to undetectable levels at perinatal or early postnatal ages. It is therefore possible that the β2-subunit promoter contains an element controlled by the activation of p[75], or that both the β2 transgene and p[75] gene are controlled by a common regulator.

In conclusion, although the promoter seems to lack some regulatory elements active in the brain, the existing regulatory elements are sufficient to allow a cell- and development-specific expression of β-galactosidase in the PNS, in the spinal cord, and in several brain structures. The promoter can also be used in assays to identify regulator proteins in neuronal tissue.

DNA Regulatory Elements

To further characterize the DNA elements involved in the transcription of the β2 subunit gene, we deleted or mutated the 1163 bp promoter and analyzed the resulting constructs by transient transfection. A repressor element present in the distal 5' end region is active in fibroblasts but not in neuroblastomas. This element thus accounts, at least in part, for the neuron-specific expression of the β2-subunit gene. Further analysis of the promoter shows that deleting 589 bp increases the activity in neuroblastomas, but not in fibroblasts (FIG. 6, compare 862E and 283E-Luci).

An NRSE/RE1 element is located at the 3' extremity of the promoter. This element has already been shown to restrict the activity of promoters in neuronal cells (Kraner et al., 1992; Mori et al., 1992; Li et al., 1993). In the 1163 bp promoter of the β2-subunit gene, point mutation of this sequence leads to a ~100 fold increase of the transcriptional activity in fibroblasts implying that this sequence is involved in the neuron-specific expression of the β2-subunit gene. Moreover, sequence comparison shows that this sequence is highly conserved in rat and human β2-subunit cDNAs (Deneris et al., 1988; Anand and Lindstrom, 1990) as well as in several promoters of genes expressed in the nervous system, such as the middle-weight neurofilament gene, the CAM-L1 gene, the Calbinbin gene, or the cerebellar Ca-binding protein gene (see Table 1B).

Deletion experiments described in FIG. 6 show that an essential activator element is present between nucleotides −245 and −95. An Sp1 binding site and an E-box could be detected in this region. Sp1 sites are ubiquitous factors, whereas E-boxes have been involved in several genetic regulatory mechanisms in muscle (see Bessereau et al., 1994 for the nAchR α1-subunit) as well as in neurons (Guillemot et al., 1993). Dyad elements have also been reported in some neuronal promoters, such as those of the Tyrosine hydroxylase gene (Yoon and Chikaraishi, 1994), the SCG10 gene (Mori et al., 1990), the GAP43 gene (Nedivi et al., 1992), or in the flanking region of the N-CAM gene (Chen et al., 1990). Results shown in Table 1A demonstrate that in neuroblastomas, the 1163 bp promoter mutated in the E-box/Dyad is significantly less active than the wild type promoter. Moreover, a gel shift assay (FIG. 7) further demonstrates that the E-box/Dyad is able to bind specific complexes. This suggests that the E-Box/Dyad is responsible for at least part of the activation of β2-subunit gene transcription. However, transactivation experiments of heterologous promoters suggest that the E-box cooperates with the Sp1 site located 27 bp upstream to positively activate transcription. This type of cooperation between an E-Box and an Sp1 binding site has already been demonstrated for the regulation of the muscle nAchR α1-subunit transcription (Bessereau et al., 1993).

In conclusion, we have shown that the β2-subunit gene is primarily regulated by negatively acting elements and by one positive element that comprises an E-box. This double regulation seems to be a general feature shared by several neuronal genes (Mandel and Mckinnon, 1993) and allows fine tuning of the transcription of neuronal genes. Moreover, our transgenic studies show that the 1163 bp promoter confers a tight neuron-specific expression, but lacks some developmental or CNS-specific regulatory elements.

DESCRIPTION OF THE FIGURES

FIG. 1: Nucleotide sequence of the region surrounding the initiator ATG of the β2-subunit gene.

Figure 3:
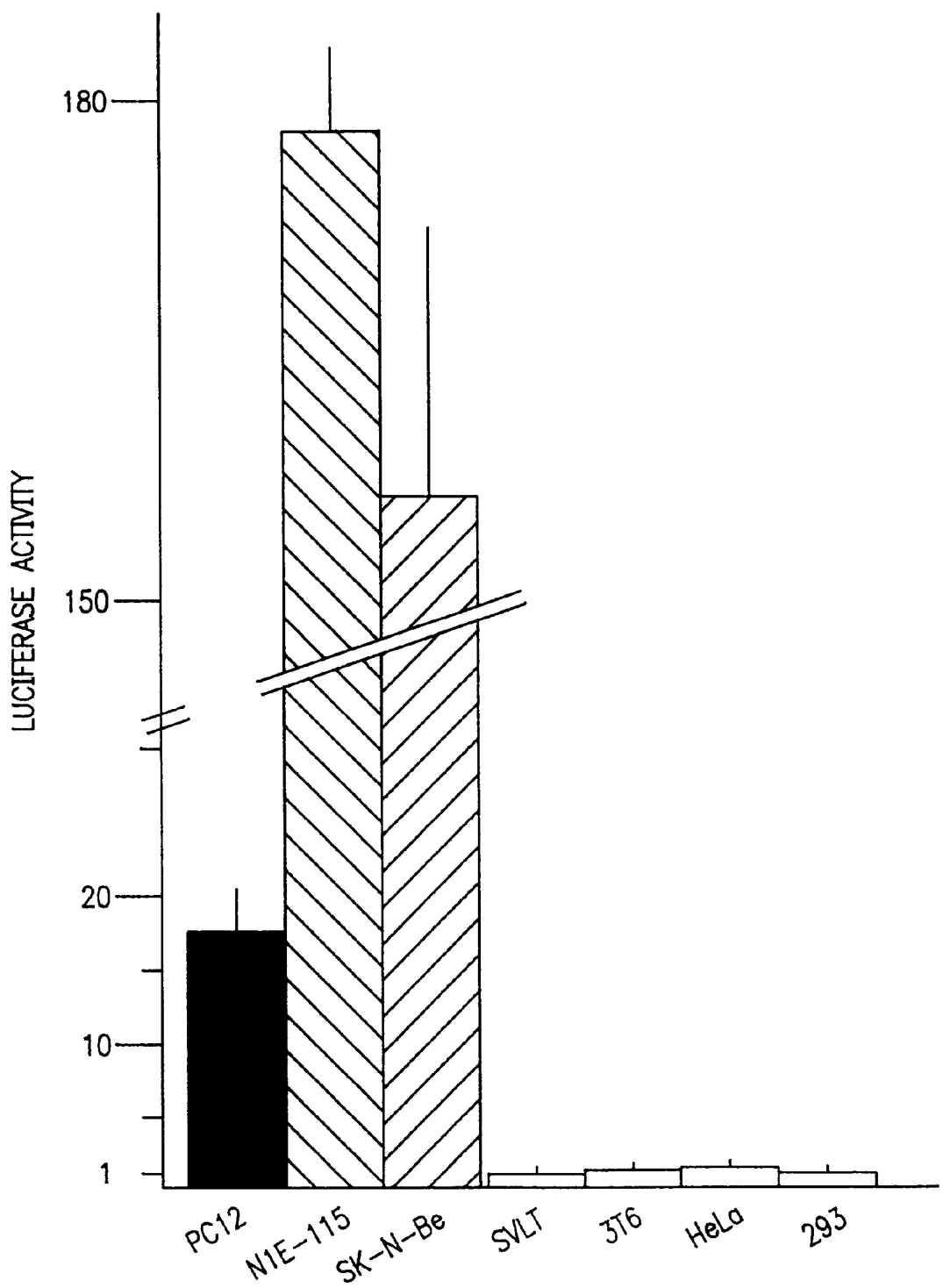

The four vertical arrowheads show the four extremities found using RACE-PCR and SLIC, corresponding to the transcription start sites. The vertical arrows indicate the position corresponding to the 5' end of the longest rat (r) and human (h) β2-subunit cDNA clones (Deneris et al., 1988). The endpoints of the deletions used in the experiments described in FIG. 3 are indicated above the sequence. Nucleotides located in the intron are typed in lower cases.

FIGS. 2(A–B): Mapping of the 5' end of the β2-subunit mRNA.

A. RNase protection experiments. Total RNA from DBA2 mouse brain (5 and 15 μg, lane 2 and 3 respectively) and yeast tRNA (15 μg, lane 1) were hybridized to a $^{32}$P-labeled RNA probe containing 158 nucleotides of intron 1, and 789 nucleotides of upstream sequences (−634/+155). The size of the protected bands were estimated according to the lower mobility in acrylamide of RNA as compared to DNA (Ausubel et al., 1994) and by comparison with the sequence of M13mp18 primed with the universal primer. The arrow on the left part of the gel points to the major protected band.

B. Identification of the transcription start site using SLIC. The lower part of the Figure shows the strategy and describes the oligonucleotides used for the SLIC or the RACE-PCR. In the SLIC experiment, a primer extension was performed using oligonucleotide pEx3. The first strand of the cDNA was subsequently ligated to oligonucleotides A5', and the resulting fragment was amplified using oligonucleotides A5'-1/p0 then A5'-2/p1. The amplified fragment was then loaded onto a 1.2% agarose gel. The gel was blotted and hybridized to oligonucleotide p2. Lane 1: 5 μg of total DBA2 mouse brain RNA. Lane 2–3: controls respectively without reverse transcriptase and without RNA. Minus: the T4 RNA Polymerase was omitted. Same result was obtained using RACE-PCR.

FIG. 3: Cell-specific expression of the β2-subunit promoter in vitro.

The luciferase activity of the plasmids were normalized to the activity of the promoterless plasmid (KS-Luci, described in Materials and Methods). RACE-PCR on mRNA extracted from SK-N-Be transfected with EE1.2-Luci, using luciferase oligonucleotides (described in Material and Methods) showed that the amplified fragment had the expected size for the correct transcription initiation site.

Figure 4A:
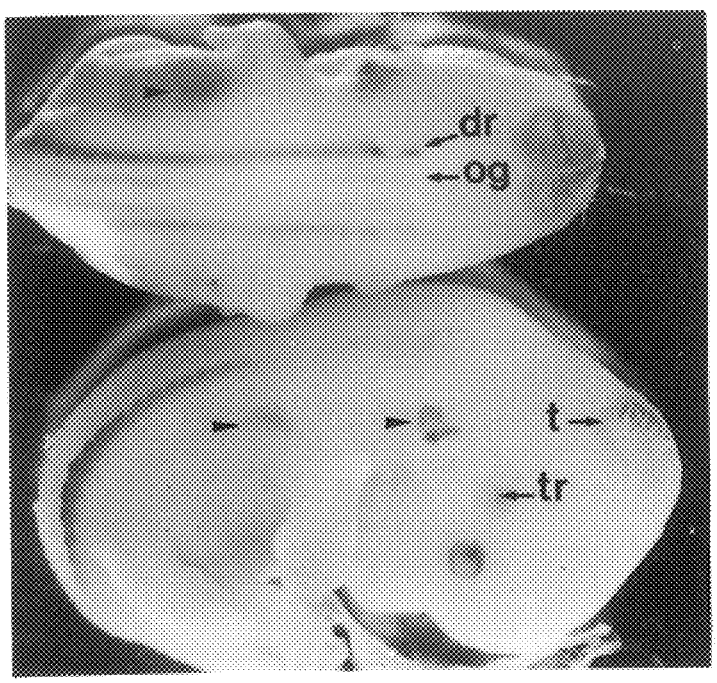
Figure 4B:
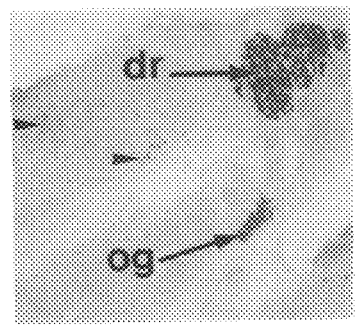

FIGS. 4(A–C): Cell-specific expression of the β2-subunit promoter in transgenic mice.

A. Whole mount coloration of E13 embryos. The arrowheads point to ectopic expression in skin muscles. B. Detection of the β-galactosidase activity in a parasagittal section of an E13 embryo at the lumbo-sacral level. Arrowheads indicate labelling in the ventral and dorsal horn of the spinal cord. C. Detection of the β2-subunit transcripts in an adjacent section of the same embryo. dr: dorsal root ganglion; t: tectum; og: orthosympathetic ganglionic chain; tr: trigeminal ganglion.

FIGS. 5(A–D): Expression of β-galactosidase in transgenic mice.

A. staining of the retina(re) and the trigeminal ganglia (tr) (E14.5). B. staining of cardiac parasympathetic ganglionic neurons (pg) (E14.5). C. transverse section of the spinal cord (P1). dr: dorsal root ganglion, og: orthosympathetic ganglion. D. Ventral view of the spinal cord (P1). The smaller arrows indicate neurons that have not been identified.

Figure 6:
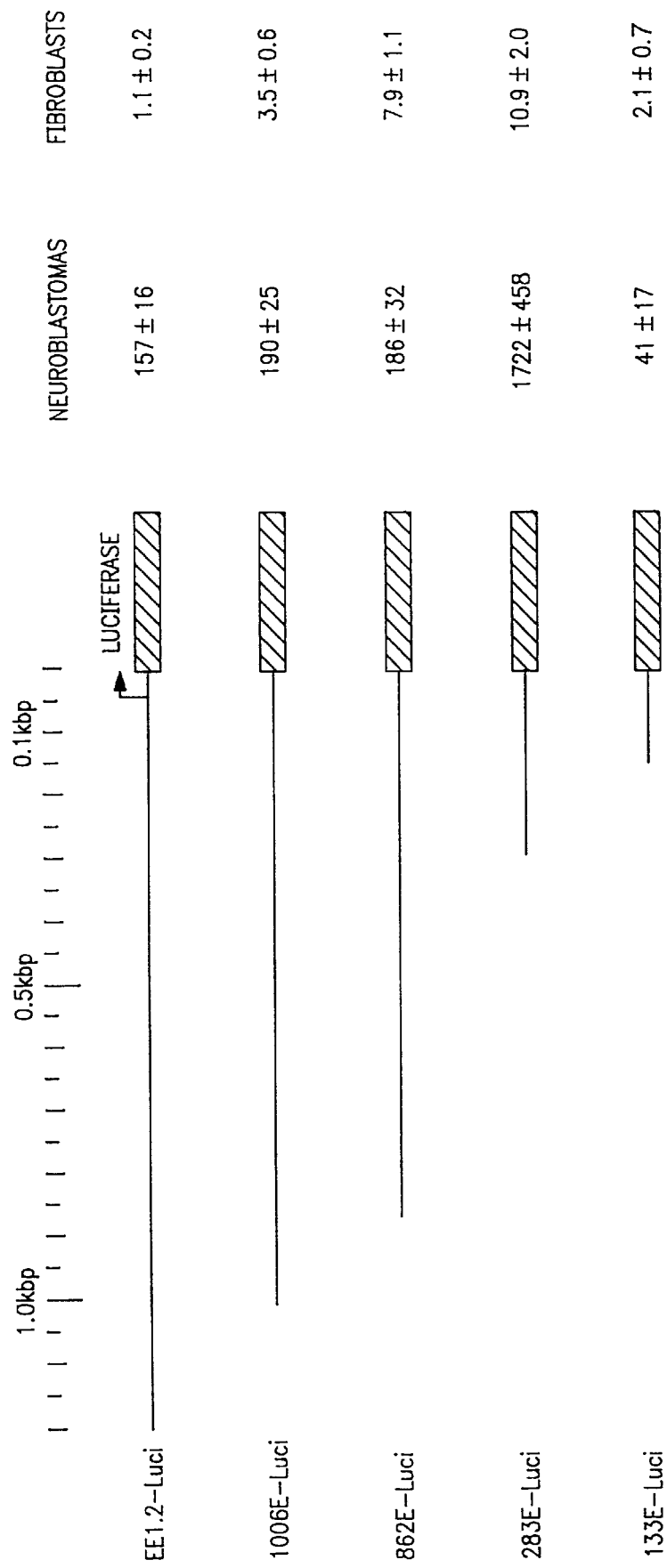

FIG. 6: Expression of the Luciferase fusion genes containing 5' end deletions of the β-subunit promoter.

Plasmids are called nnnE-Luci, where nnn is the size in nucleotides of the insertion, and E is the 5' end restriction site (Eco47III). The arrow indicates the transcription start site. The activities of EE1.2-Luci are from FIG. 3.

Figure 7:
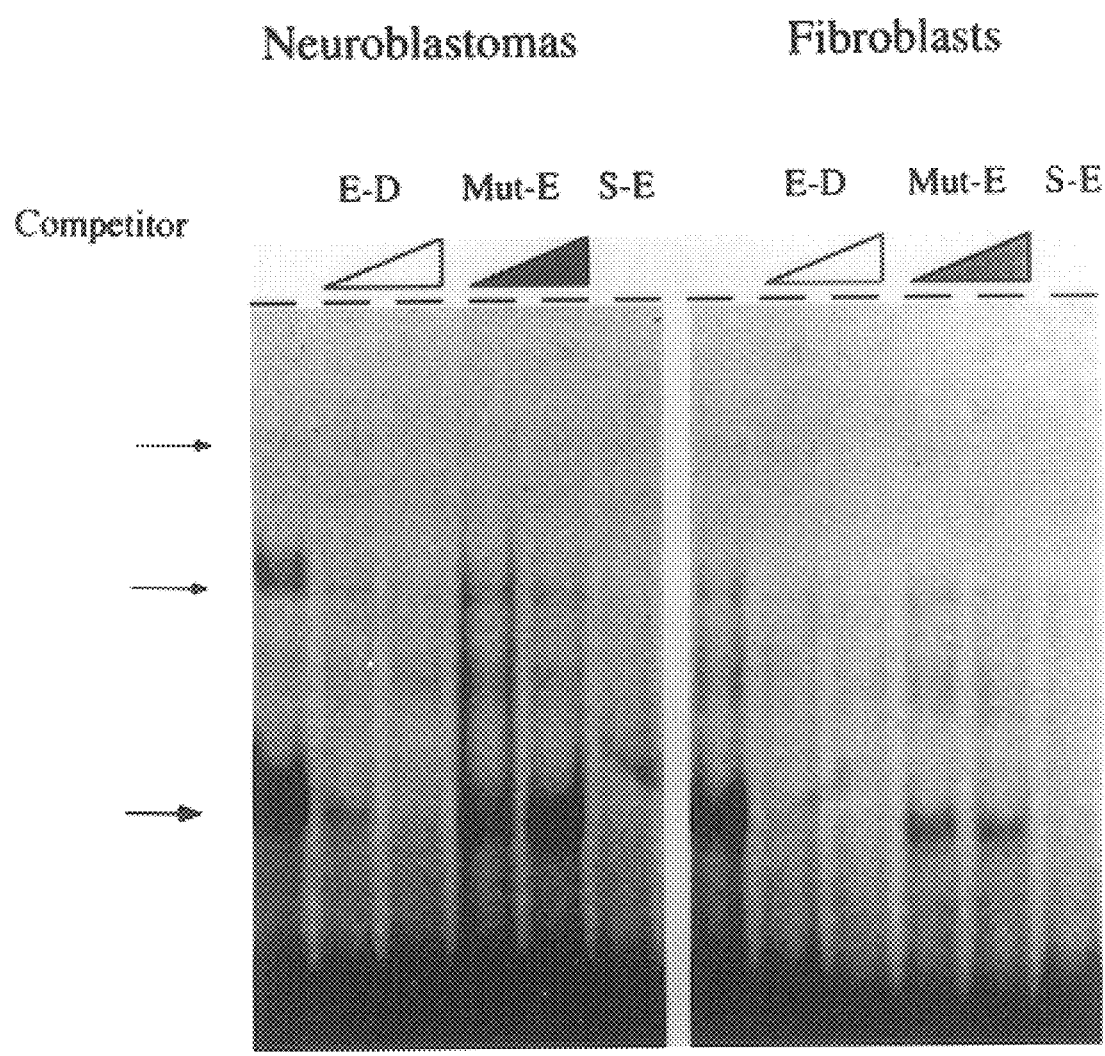
Figure 8A:
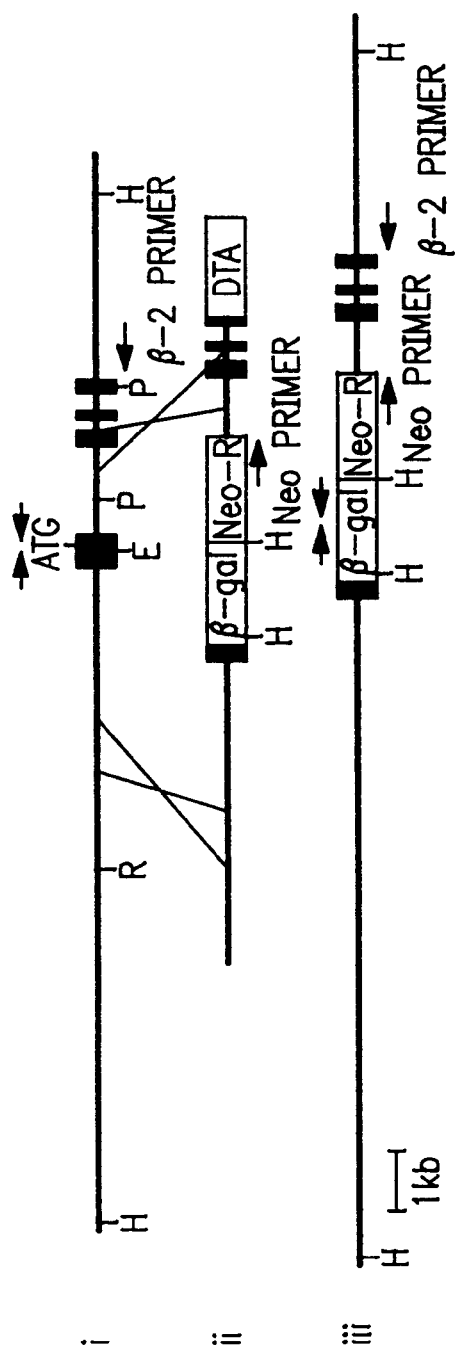
Figure 8B:
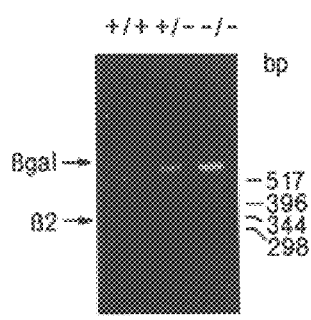
Figure 8C:
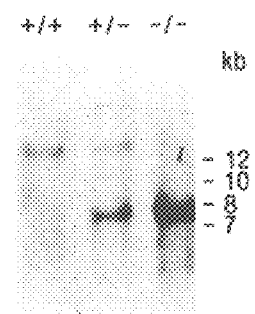
Figure 8D:
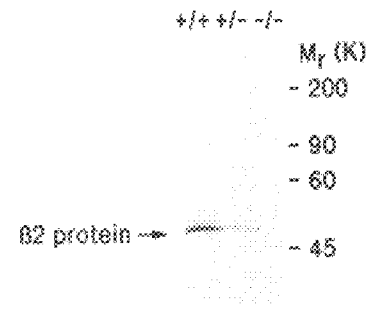

FIG. 7: Gel shift experiment. Autoradiogram of the mobility shift experiment. The probe used was a $^{32}$P labelled double stranded E-D oligonucleotide. This oligonucleotide carries only the E-Box/Dyad element, whereas the oligonucleotide S-E carries the Sp1 binding site as well as the E-Box/Dyad element. The competitor oligonucleotides were used in 10- and 100-fold molar excess, except for S-E that was used only in 100-fold molar excess.

FIGS. 8(A–D): Disruption of the gene encoding the β2-subunit of the neuronal nAChR. a-i, Normal genomic structure of the mouse β2-subunit gene. Portion of exon one removed by the recombination event is shaded in light grey. ATG-initiator methionine. Boxes represent exons I–IV. a-ii, Targeting replacement vector used to disrupt the endogenous β2-subunit gene. Initiator methionine and the rest of the first exon were replaced with the coding region of NLS-lacZ and the MC1 neo$^R$ expression cassette[25]. The construct was able to direct lacZ expression after stable transfection of PC12 cells (not shown), but lacZ expression was never detected in recombinant animals, despite the lack of obvious recombination in the lacZ DNA. Diphtheria toxin-A gene (DTA)[26] was used to select against random integration. a-iii, Structure of the mutated β2-gene. Restriction sites: H, HindIII; R, EcoRI; E, Eco47III; P, PstI. Black arrows, primers used to detect recombination events in embryonic stem (ES) cells. Grey arrows, primers used to detect the wildtype or mutated β2 genes. b, PCR analysis of tail DNA from a +/+, +/− and a −/−mouse. c, Southern blot analysis of tail DNA restricted with HindIII from the same mice analyzed in panel b. d, Western blot analysis of total brain protein using a monoclonal antibody raised against the β2-subunit.

Methods a, The β2-targeting vector was constructed by inserting a multiple cloning site (MCS) into the MC1 neo cassette (GTC GAC GGT ACC GCC CGG GCA GGC CTG CTA GCT TAA TTA AGC GGC CGC CTC GAG GGG CCC ATG CAT GGA TCC (SEQ ID NO:30)). A 4.1 kB EcoRI-Eco47III β2-genomic fragment 5' to the ATG and a 1.5 kB PstI β2-genomic fragment starting within the first intron of the β2-gene were cloned into the MCS. HM1[27,28] embryonic stem cells (5×10 ) were transfected with the linearized targeting vector by electroporation as described[25]. Twenty-four surviving G418-resistant clones were screened by PCR β2-primer-GCC CAG ACA TAG GTC ACA TGA TGG T (SEQ ID NO:31); neo-primer-GTT TAT TGC AGC TTA TAA TGG TTA CA (SEQ ID NO:32)). Four were positive and were later confirmed by Southern blot analysis. Clones were injected into 3.5-day-old blastocysts from non-agouti, C57BL/6 mice and planted in receptive females. All resulting male chimaeric mice were mated to F1, C57BL/6xDBA/2 non-agouti females. Of 15 chimaeras, one showed germ-line transmission. β2 +/−heterozygotes were mated and offspring were evaluated by PCR analysis (panel b). b, PCR was 35 cycles of 94°/1 min, 65°/2 min and 72°/1 min. c, Southern blotting was performed as described[29]. The 1.5 kB PstI genomic fragment used for the targeting construct was labelled by random priming. d, Western blotting was performed as described[29] using monoclonal antibody 270[11].

FIGS. 9(A–B): Mapping of the neuronal nAChR in mouse brain using in situ hybridization and tritiated nicotine binding. A, In situ hybridization using antisense oligonucleotide probes based on the sequence of the cDNAs encoding the β2-, α4- and β4-subunits of the nAChR to detect their respective mRNAs in serial sections from the brains of β2 +/+, +/− and −/−mice. Midthalamic sections are shown. White arrows indicate the MHb labelled by the β4-antisense oligonucleotide. B, Receptor autoradiography using tritiated nicotine revealing high affinity binding sites in the brains of wildtype, heterozygous and β2-mutant mice. Representative sections at the level of the striatum, thalamus and tectum are shown.

Methods

A, In situ hybridization was performed as follows:

In situ hybridization procedure. Frozen tissues were cut at the cryostat [14 μm thick sections), thaw mounted on poly-1-lysine coated slides and stored at −80° C. for 1–3 days. The procedure was carried out according to Young et al. (1986). Briefly, sections were fixed with 4% paraformaldehyde for 5 min. at room temperature, washed in phosphate buffered saline (PBS) and then acetylated and delipidated in ethanol and chloroform (5 min.). They were prehybridized for 2–4 h at 37° C. under parafilm coverslips. The composition of the prehybridization and hybridization mixtures was 50% formamide, 0.6M NaCl, 0.1M dithiothreitol, 10% dextran sulfate, 1 mM ethylenediaminetetraacetic acid (EDTA), 1XDenhardt's solution (50x=1% bovine serum albumin/1% Ficoll/1% polyvinylpyrrodlidone), 0.1 mg/ml polyA (Boehringer), 0.5 mg/ml yeast RNA (Sigma), 0.05 mg/ml herring sperm DNA (Promega) in 0.02M Tris-HCI, pH 7.5. Probes were applied at a concentration of 2000–3000 Bcq/30 μl section (corresponding to around 15 fmol/section). After removal of coverslips and initial rinse in 2x standard saline citrate (SSC) solution (3M NaC1/0.3M sodium citrate) at room temperature (two time for 5 min.), sections were washed four times for 15 min in 2x SSC/50% formamide at 42° C. and, then, two times for 30 min in 1x SSC at room temperature. 1 mM dithiothreitol was added to all washing solutions. After rinsing in ice-cold distilled water and drying, they were exposed for 10–20 days to Hyperfilm βmax (Amersham) and then to a photographic emulsion (NTB2, Kodak) for 1–2 months.

Analysis of histological preparations. The analysis of the labelling pattern for the different mRNAs was carried out both on film and emulsion autoradiograms. Identification of anatomical structures was carried out after counterstaining of the serial sections of the entire embryos with toluidine blue. Definition of anatomical areas in the brain and recognition of peripheral nervous system (PNS) structures was based on different atlases, including The Rat Brain in Stereotaxic Coordinates (Paxinos and Watson, 1986), the Atlas of Developing Rat Brain (Paxinos et al. 1991), the Atlas of Mouse Development (Kaufman, 1992), and the Atlas of the Prenatal Mouse Brain (Schambra et al., 1992). For cranial nerve ganglia development, the plates and descriptions from Altman and Bayer (1982) were consulted. In order to confirm the identification of some central and peripheral structures (e.g., cranial nerve motor nuclei, autonomic motor ganglia) in situ hybridization for choline acetyltransferase was performed on some sections.

A score from 1+ (low intensity) to 3+ (high intensity) was assigned to the labelling of the anatomical structures based on the subjective evaluation of two experimenters. Background labelling was considered the density of grains in nonneural tissues high cellularity (such as the liver and muscles) or with high density of extracellular matrix (such as cartilage) or the density of labelling over neural structures after displacement with 20× cold probe. In the absence of grain counting at the cellular level, the scores must be regarded with caution. For instance, decreases in labelling intensity of a developing structure may be due to dispersion of positive cells in the structure caused by multiplication of negative cells or formation of neuronal processes. Though the oligonucleotides had the same length and they were labelled according to the same protocol, no attempt to compare the signal intensity or different transcripts was made. Unless specified otherwise, the labeling shown in the pictures has been obtained by using oligonucleotides no. 31 (α3), 47 (α4), 51 (12), and 62 (α4) (see Table 1 for oligonucleotide characteristics). Specificity controls. For each mRNA, two to four oligonucleotides were selected in unique parts of the sequence (e.g., the putative cytoplasmic loop between M3 and M4 for nAChR subunits). An initial assessment of the specificity was performed by searching for possible homology with other known sequences in Genbank/EMBL. As histological tests for specificity were considered the following: 1. Two or more oligonucleotide probes for each mRNA gave the same hybridization pattern (FIG. 1). 2. The pattern of labelling in central structures in the adult rat was in agreement with that observed by other authors (Wada et al., 1989; Dineley-Miller and Patrick, 1992). 3. Given that most oligonucleotides used were 45-mers with similar GC content (Table 1), each oligonucleotide probe constituted a control for the specificity of the others. 4. The addition to the hybridization mixture of a 20-fold excess of cold probe produced a complete disappearance of the labelling (FIG. 2).

The oligonucleotide probes used fulfilled all these criteria, with the exception of the four probes against α3 mRNA, which did not satisfy criterion 2. Previous studies based on cRNA probes showed a relatively widespread distribution of this subunit mRNA in adult rats, notably high levels in the cerebral cortex layer IV, entorhinal cortex layer II, anterior and ventral thalamic nuclei, medial and lateral geniculate nuclei, medial habenula, posterior hypothalamus and supramammillary nuclei, pineal gland, motor nuclei of the V and VII nerves, locus coeruleus, nucleus ambiguus, and area postrema (Wada et al. 1989). At variance with these observations, in adult rats we could detect high levels of α3 mRNA signal only in the medial habenula, intermediate in the pineal gland, area postrema, motor nucleus of the V nerve and cerebellum, low in a few thalamic nuclei and locus coeruleus. Part of the discrepancy may be ascribed to a lower sensitivity of oligonucleotide probes versus riboprobes. However, considering the difficulty of carrying out specificity controls for cRNA probes, especially when hydrolysis of the probe is performed in the histological procedure (Wada et al., 1989), it is possible that some labelling previously attributed to α3 mRNA actually derives from hybridization to other (nAChR-related) RNA sequences. Oligonucleotides: β2: (SEQ ID NO:1) 5'-TCG CAT GTG GTC CGC AAT GAA GCG TAC GCC ATC CAC TGC TTC CCG-3'; α4 (SEQ ID NO:2): 5'-CCT TCT CAA CCT CTG ATG TCT TCA AGT CAG GGA CCT CAA GGG GGG-3'; β4 (SEQ ID NO:3): 5'-ACC AGG CTG ACT TCA AGA CCG GGA CGC TTC ATG AAG AGG AAG GTG-3'. B, $^3$H-nicotine binding was performed as described by Clarke et al[30]. Fourteen μm coronal sections were incubated at room temperature for 30 min. in 50 mM Tris pH 7.4/8 mM $CaCl_2$/4 nM $^3$H-L-nicotine. Nonspecific binding was evaluated in the presence of 10 μM L-nicotine bitartrate. Following incubation, sections were rinsed 2×2 min. in ice cold PBS and briefly rinsed in ice cold water. Slides were exposed for 60 days to Hyperfilm $^3$H.

FIGS. 10(A–B): Patch clamp recording of nicotine evoked currents in the MHb and anterior thalamus of β2 +/+ and +/+mice. A, Representative recordings from cells in the MHb and the anterior thalamus of wildtype and β2 –/–mice. The off-rate of the agonist is significantly greater in the MHb than in the anterior thalamus, resulting in a different kinetics of response in the two structures. The response to nicotinic agonists of the MHb is maintained in β2 –/–animals, while the response to nicotinic agonists of the anterior thalamus is completely abolished in β2 –/–mice. B, table of responses to nicotinic agonists in various nuclei of β2 +/+ and –/–mice.
Methods Coronal slices were obtained from the thalamus of 8–12 day old mice using a Dosaka slicer in ice cold ACSF medium (125 mM NaCl/26 mM $NaHCO_3$/25 mM Glucose/ 1.25 mM $NaH_2PO_4$/2.5 mM KCl 2.5/2 mM $CaCl_2$/1 mM $MgCl_2$ pH 7.3). Slices were maintained in the same medium for 1–8 hours. Cells in slices were visualized through a Zeiss microscope. Whole cell recordings were obtained with 2–4 MOhm hard-glass pipettes containing 150 mM CsCl/10 mM EGTA/10 mM HEPES/4 mM di-sodium ATP/4 mM $MgCl_2$ pH adjusted to 7.3 with KOH. Five to ten sec. pulses of drug were applied rapidly to the cell through a 50 μM diameter pipette above the slice, fed by gravity with a solution containing 150 mM NaCl/10 mM Hepes/2.5 mM KCl/2 mM $CaCl_2$/1 mM $MgCl_2$. Recordings were made in the presence of CNQX (5 μM) and of the $GABA_A$ antagonist SR-95531 (10 μM). Currents were recorded with an Axopatch ID (Axon Instrument) patch amplifier, digitized on a Compaq PC and further analyzed with the PClamp program (Axon Instrument).

Figure 11A:
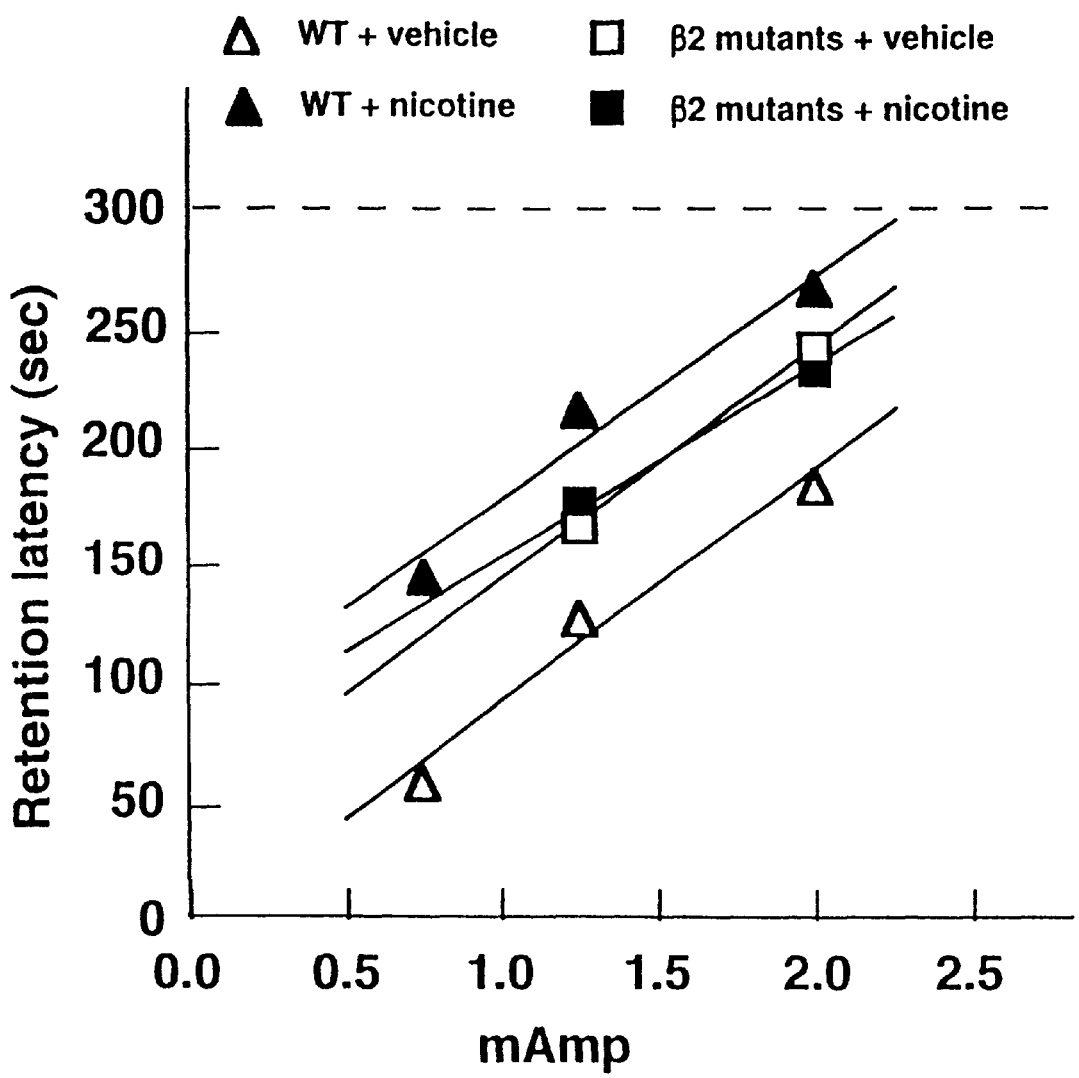
Figure 11B:
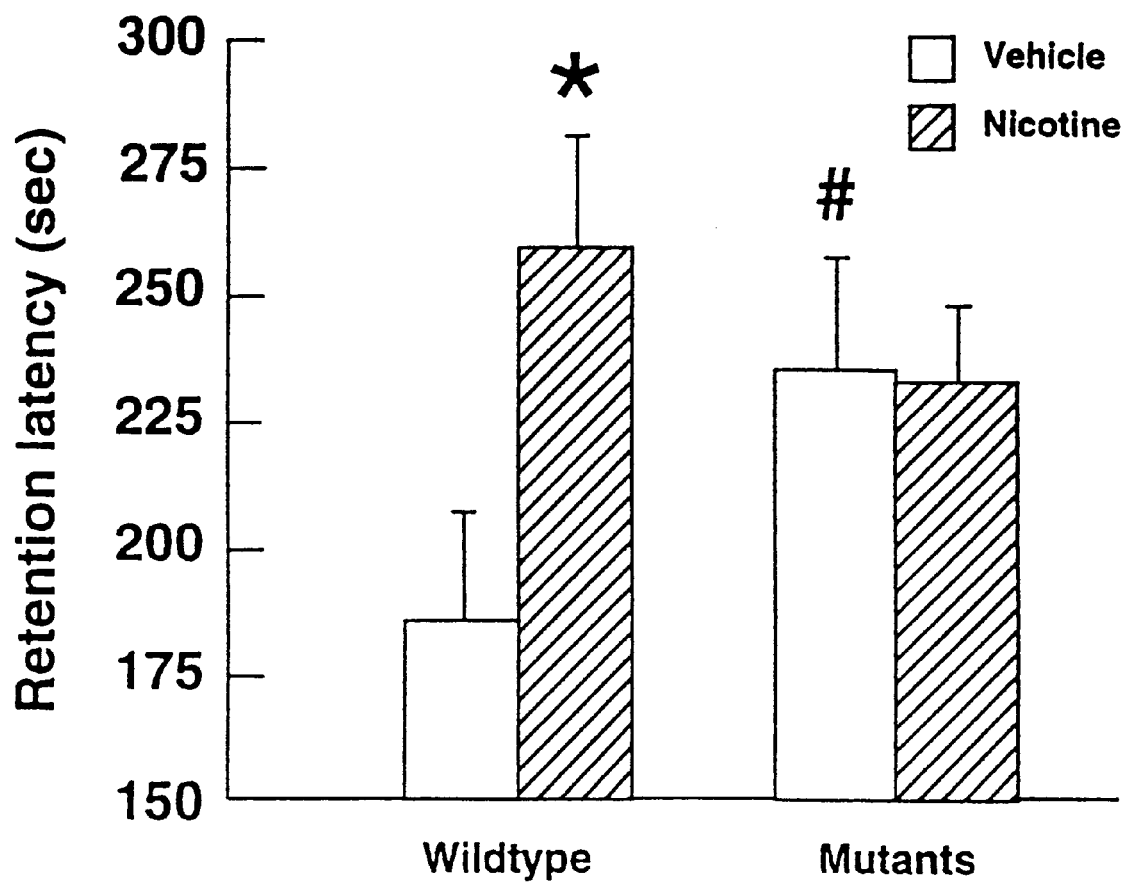

FIGS. 11(A–B): Performance of β2 –/–mice and their wildtype siblings on the passive avoidance test. A, response to various levels of footshock in retention test following a post-training injection of either vehicle or nicotine (10 μg/kg). Average step-through latency during the training trial was 17.0+/–3.6 sec for mutant mice and 15.0+/–3.5 sec for their nonmutant siblings. B, bar graph showing the difference in retention latency between wildtype and homozygous β2 mutant mice injected with either vehicle or nicotine (10 μg/kg) at foot shock intensity of 2.00 mAmp. Data are represented as means +/–S.E.M. of the following groups: wildtype+vehicle (n=27); wildtype+nicotine (n=23); β2-mutant mice+vehicle (n=17); β2-mutant mice+nicotine (n=17). Statistical analysis was performed using a mixed factorial analysis of variance followed by a-posteriori testing of simple effects. #, $p <0.05$, wildtype vs mutant mice following vehicle injection; *, $p <0.01$, nicotine vs vehicle in wildtype mice.
Methods Passive avoidance test was performed as described in the text, according to Nordberg and Bergh[20] and Faiman et al[20]. Nicotine (bitartrate, Sigma) was freshly dissolved in PBS. IP injection of the same volume of either nicotine or vehicle immediately followed footshock during the training trial.

Figure 12:
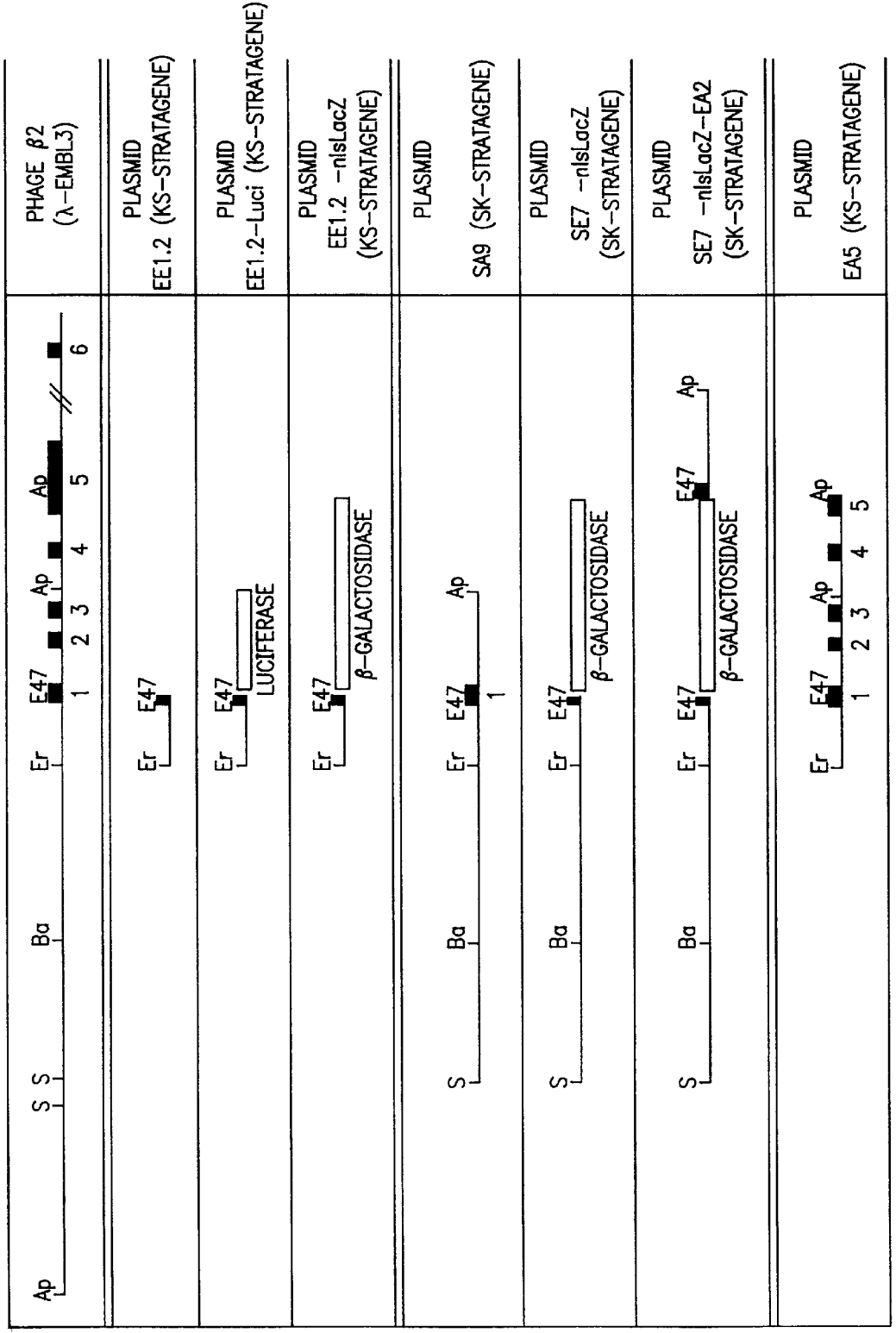

FIG. 12: Phage and plasmids containing all or part of the β2-subunit gene and the promoter. In the names of the plasmids, the numerals indicate the size of the fragment and the letters indicate the restriction sites used to generate it.

DETAILED DESCRIPTION

The descriptions and examples below are exemplary of the embodiments and scope of this invention. The invention is not limited to the scope of this description. Furthermore, this description together with the accompanying sections of this specification and the material incorporated by reference enables the practice of all of the claims which follow.

The examples and embodiments that follow of course can be modified by techniques known in the art. Variations in the nucleic acid sequences described or claimed can be produced by known methods without altering the effects or advantages the inventors have shown. Such variations are therefore included within the scope of this description and invention.

Materials and Methods

Isolation of Genomic Clones

The PCX49 plasmid (Deneris et al., 1988) containing the entire rat cDNA (kindly provided by Drs. J. Boulter and S. Heinemann, The Salk Institute, San Diego, Calif.) was cut with EcoRI, the ~2.2 kb fragment was isolated and used as a probe to screen an EMBL3 bacteriophage library of mouse DBA2 genomic DNA. One unique clone was obtained spanning ~15 kb of DNA upstream and ~5 kb downstream from the first exon. FIG. 1 shows the nucleotide sequence of 1.2 kb upstream from the initiator ATG.

Hybridization conditions can be modified by known techniques[29] to determine stringent conditions for this probe. Changes in the hybridization conditions such as temperature (from about 45° C. to about 65° C.) and SSC buffer concentration (from about 0.1×SSC to about 6×SSC), as well as changes in the temperature of and the buffer for the washing conditions can be made to develop sufficiently stringent conditions that allow hybridization to the β2-subunit sequences. Other related sequences can thus be isolated from other libraries based on this hybridization procedure. Human sequences will be isolated by using hybridization conditions such as 45° C. and 6×SSC.

Three deposits were made on Dec. 13, 1994 at the Collection Nationale de Cultures de Microorganismes (CNCM), Institut Pasteur, 25 Rue du Docteur Roux, 75724 PARIS CEDEX 15, France. A phage, λβ2 nAchR, is deposited under the accession number I-1503. This phage contains 15–20 kb of genomic DNA including the promoter sequences and the coding sequences for all of the exons of the murine β2-subunit of neuronal nAchR. Two E.coli cultures bearing plasmids have also been deposited. Plasmid pSA9 in E. coli DH5α has accession number I-1501 and contains 9 kb of murine genomic DNA including the regulatory sequences and regions coding for exons 1, 2 and 3 of the β2-subunit. Plasmid pEA5 in E. coli DH5α has accession number I-1502 and contains 5 kb of murine genomic DNA including a region of about 1.2 kb upstream of the Eco47-III site and a region coding for exons 1 to 5 of the β2-subunit. The inventors intend to deposit the nucleotide sequence data reported here in the EMBL, GenBank and DDBJ Nucleotide Sequence Databases under the accession number: X82655.

Mapping of the Transcription Initiation Site

For the mRNA mapping, we used different batches of total RNA extracted from DBA2 embryos at stage E13 or E15. The RNA samples were first digested with DNase I to avoid DNA contamination.

RNase protection. An XbaI/PstI fragment containing part of intron 1 was inserted into Bluescript SK (Stratagene). The plasmid was then linearized by BglII, and an RNA probe was synthesized using the T7 promoter. The protection experiments were then performed as described in Ausubel et al. (1994).

RACE-PCR (Frohman et al., 1988). The mRNA was hybridized 5 minutes at 80° C. with 10 pmol of primer. The synthesis of the cDNA was performed using 400 u MMLV (Gibco) for 45 minutes at 37° C. in the buffer recommended by the supplier. After a phenol/chloroform extraction, the cDNA was ethanol precipitated. The terminal transferase reaction was performed in 0.2 M potassium cacodylate; 25 mM Tris-HCl pH 6.6; 25 mg/ml BSA; 1.5 mMCoCl$_2$; 50 nM DATP and 50 u Terminal transferase (Boehringer) for 30 minutes at 37° C.. After phenol/chloroform extraction and ethanol precipitation, one tenth of the terminal transferase reaction was amplified using Promega's Taq DNA polymerase (30 cycles, 1 minute at: 94° C.; 55° C.; 72° C.). The amplified fragment was then loaded on an agarose gel. The gel was blotted and hybridized to oligonucleotide p2. We used pEx2 as a primer for cDNA synthesis, and p0/BEpT for PCR to map mRNA from brain. OLUCI3 (synthesis of cDNA) and OLUCI2/BEpT (PCR) were used to map mRNA from transfected cells.

SLIC (Dumas Milnes Edwards et al., 1991). The cDNA was first synthesized from 5 µg total RNA using pEx3 (6 pmol) as a primer in 50 mM Tris-HCl pH 8.3; 8 mM KCl; 1.6 mM MgCl$_2$; 5 mM spermidine; 0.5 mM dNTP; 1 u/µl RNasin; 0.1 mg/ml BSA; 70 mM β-mercaptoethanol; 80 u AMV reverse transcriptase (Promega) at 42° for 45 minutes. The RNA was subsequently degraded in NaOH. The first strand of the cDNA was then ligated with the oligonucleotide A5'. The resulting single stranded cDNA was then submitted to two rounds of PCR amplification with oligonucleotides A5'-1/p0 and A5'-2/p1 (35 cycles 94° C. 1 minute; 60° C. 30 seconds; 72° C. 45 seconds).

The sequence of the oligonucleotides were the following:

A5' (SEQ ID NO:4):
5'-CTGCATCTATCTAATGCTCCTCTCGCTACCTGC TCACTCTGCGTGACATC

A5'-1 (SEQ ID NO:5):
5'-GATGTCACGCAGAGTGAGCAGGTAG

A5'-2 (SEQ ID NO:6):
5'-AGAGTGAGCAGGTAGCGAGAGGAG p0 (SEQ ID NO:7):
5'-CCAAAGCTGAACAGCAGCGCCATAG p1 (SEQ ID NO:8):
5'-AGCAGCGCCATAGAGTTGGAGCACC p2 (SEQ ID NO:9):
5'-AGGCGGCTGCGCGGCTTCAGCACCACGGAC pEx2 (SEQ ID NO:10):
5'-GCCGCTCCTCTGTGTCAGTACCCAAAACCC pEx3 (SEQ ID NO:11): 5'-ACATTGGTGGTCATGATCTG
BEpT (SEQ ID NO:12): 5-GCGGGATCCGAATTC(T)$_{21}$A/C/G

OLUCI3 (SEQ ID NO:13):
5'-CGAAGTATTCCGCGTACGTGATG

OLUCI2 (SEQ ID NO:14):
5'-ACCAGGGCGTATCTCTTCATAGC

Construction of Plasmids

KS-Luci: The HindIII/KpnI restriction fragment of the pSVOAL plasmid (de Wet et al., 1987) was subcloned in the corresponding site of Bluescript KS. The most 5' EcoRI/BsmI (45 bp) fragment of the Luciferase gene was then deleted according to (de Wet et al., 1987) and replaced by a Sal I site. The 342 bp PvuII/HindIII restriction fragment of SV40 containing the polyadenylation sites was subsequently subcloned into the EagI sites using adaptors.

EE1.2-Luci: The 1.2 kbp EcoRI/Eco47II fragment of the λβ2 phage was inserted in the EagI/SalI sites of KS-Luci using adaptors. The 5' end deletions of the promoter were obtained using Bal3.1 exonuclease as in Current Protocols in Molecular Biology (Ausubel, et al., 1994).

The mutations were introduced using the Sculptor kit (Amersham). In the NRSE/RE1 sequence, the mutated sequence was: +24 (SEQ ID NO:15) ACCAC<u>TT</u>ACA instead of (SEQ ID NO:16) ACCAC<u>GG</u>ACA, as this mutation was shown to reduce the activity of the NRSE element (Mori et al., 1992). In the E-box sequence, the mutated sequence was: −120 (SEQ ID NO:17) TC<u>CT</u>CAGG instead of (SEQ ID NO:18) TC<u>CA</u>CTTG. FIG. 7 shows that a nuclear protein is able to bind to the wild type sequence, but not to the mutated sequence.

Transfection of Cells

Neuroblastomas N1E115, human SK-N-Be, HeLa and 3T6 fibroblasts, 293 Human kidney cells and SVLT striatal cells (Evrard et al., 1990) were grown in DMEM+10% FCS supplemented with 1% glutamine and 1% streptomycin. PC12 cells were grown in DMEM+10% HS+5% FCS supplemented with 1% glutamine and 1% streptomycin.

Cells were plated at $10^5$ to $4\times10^5$ cells/60 mm$^2$ plates. The next day cells were transfected in 750 μl of DMEM+2% Penicillin/Streptomycin for 5 to 12 hours with 1 μg DNA mixed with 2.5 μl of Transfectam (IBF/Sepracor) in 150 mM NaCl. The Luciferase activity was measured 48 hours later. DNA was prepared using Qiagen or Wizard prep (Promega) kits. When plasmid activities were compared, all plasmids were prepared the same day. At least two different DNA preparations were tested for each plasmid. All transfections were done in duplicate and repeated at least three times.

Production of Transgenic Mice

The luciferase gene from EE1.2-Luci was excised and replaced by the nlsLacZ gene (Kalderon et al., 1984). The β2-promoter/nlsLacZ fragment was electroeluted from a TAE agarose gel then further purified by ethanol precipitation, and finally resuspended in Tris-HCl 10 mM pH 7.5; EDTA 0.1 mM. The DNA solution (3 ng/ml) was injected into fertilized oocytes of C57BL6xSJL hybrids. Staining of tissues was performed as described in Mercer et al., 1991.

See also the methods under FIG. 8.

Gel Shift Assay

Oligonucleotides were labeled either with γ[$^{32}$P]ATP and T4 polynucleotide kinase, or with α[$^{32}$P]CTP and Klenow enzyme as in Current Protocols in Molecular Biology. Nuclear extracts were prepared from ≃$10^7$ cells as described (Bessis et al., 1993). For binding, 1 nmol of labeled oligonucleotide was mixed with 0,5 μg of protein extract in 10 mM Hepes pH 8, 10% glycerol, 0,1 mM EDTA, 0.1 M NaCl, 2 mM DTT, 0.1 mg/ml BSA, 4 mM MgCl$_2$, 4 mM spermidine, 1 mM PMSF, 1 μg polydIdC in 20 μl. The reaction was incubated for 10 minutes on ice. The DNA-protein complexes were then analyzed on a 7% polyacrylamide gel.

The oligonucleotides used in this experiments were double stranded with the following sequences (the underlined nucleotides are changed between the mutated and the wild type oligonucleotides):

E-D: (SEQ ID NO:19) 5'-TCCTCCCCTAGTAGTTCC AC<u>TT</u>GTGTTCCCTAG

Mut-E: (SEQ ID NO:20) 5'-CCTCCCCTAGTAGTTCC TC<u>AG</u>GTGTTCCCTAGA

S-E: (SEQ ID NO:21) 5'-CTAGCTCCGGGGCGGAGACTCCTCCCC TAG-TAGTTCCACTTGTGTTCCCTAG

Results

Figures 2A, 2B:
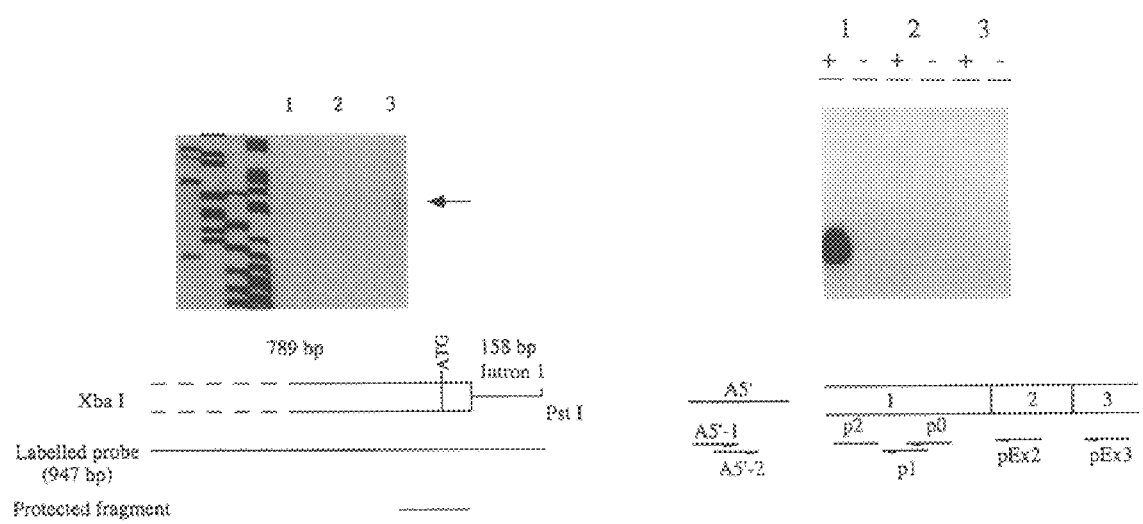

Characterization of the 5' Flanking Sequences of the Gene Encoding the β2-subunit A γ phage containing the gene encoding the β2-subunit was cloned and a region surrounding the initiator ATG was sequenced (FIG. 1). The transcription initiation site was first mapped by RNase protection (FIG. 2A). This method allowed us to detect at least three initiation sites. However, minor additional start sites might not have been detected in these experiments. The size of the main protected band was estimated at about 150 nucleotides. To confirm and locate the initiation sites more precisely, we performed both RACE-PCR (Rapid Amplification of cDNA Ends; Frohman et al., 1988) and SLIC (Single Strand Ligation of cDNA; Dumas Milnes Edwards et al., 1991) which consist in the amplification of the primer extension product (FIG. 2B). Both techniques allowed us to subclone and sequence the same fragments corresponding to the four initiation sites described in FIG. 1. It is probable that the −13 start site is very rare and was not detected by RNase mapping.

Analysis of the sequence of the flanking region (FIG. 1) revealed several consensus DNA binding elements: an Sp1 site (−146), a cAMP responsive element binding (CREB) site (−287; Sassone-Corsi, 1988), a nuclear receptor response element (−344 to −356; Parker, 1993), a GATA-3 site (−1073; Ko and Engel, 1993), and a weakly degenerate Octamer motif (−522). Moreover, an E-box (−118) contained in a dyad symmetrical element could be recognized. The proximal region (−245 to +82) also has an unusually high GC content (67%) and a high number of dinucleotide CpG that may have some regulatory significance (Antequera and Bird, 1993). Finally, a 20 bp sequence identical to the NRSE (Neural Restrictive Silencer Element; Mori et al., 1992) or RE1 (Restrictive Element; Kraner et al., 1992) sequence was found in the 3' end of the 1.2 kbp fragment (+18 to +38).

A 1.2 kbp Fragment of Flanking Sequence of the β2-subunit Gene Promotes Neuron-Specific Expression in Vitro A construct was generated containing the 1163 bp EcoRI/Eco47III fragment (from −1125 to +38) of the β2-subunit 5' flanking region fused to the Luciferase gene (de Wet et al., 1987) (plasmid EE1.2-Luci). The polyadenylation sites of SV40 were inserted upstream from the β2-subunit sequences to avoid readthrough. The transcriptional activity of the plasmid EE1.2-Luci was then tested by transient transfection into pheochromocytoma (PC12) cells, neuroblastoma cell lines NIE 115 and SK-N-Be, SVLT, a striatal cell line (Evrard et al., 1990), NIH3T6 or HeLa fibroblasts and human kidney cell line 293. Using RT-PCR, we verified that the neuroblastomas and the PC12 cells normally express the β2-subunit mRNA but not the striatal SVLT cell lines or the 3T6 fibroblasts. FIG. 3 shows that in PC12 cells and neuroblastomas, the 1.2 kbp fragment is 20 to 180-fold more active in mediating transcription of the reporter gene than in the other cell lines. In fibroblasts, 293 cells and SVLT cells, the transcriptional activity of the 1.2 kbp fragment is not significantly higher than that of the promoterless vector (FIG. 3). Therefore, the β2-subunit promoter is not active in these cell lines. These in vitro transfection experiments demonstrate that the 1163 bp fragment mimics the expression pattern of the endogenous β2-subunit gene, and thus contains a cell-specific promoter.

The 1163 bp Promoter in Transgenic Mice

To test the 1163 bp promoter in vivo, the EcoRI/Eco47III fragment was linked upstream from the nls-β-galactosidase reporter gene (Kalderon et al., 1984). The polyadenylation signals from SV40 were ligated downstream of the coding sequences. The resulting 4.7 kb fragment was subsequently microinjected into the male pronuclei of fertilized eggs from F1 hybrid mice (C57B16xSJL). DNA extracted from the tails of the offspring was analyzed for the presence of the β-galactosidase gene by the polymerase chain reaction (PCR). Three independent founders were obtained and analyzed for expression.

Figure 4C:
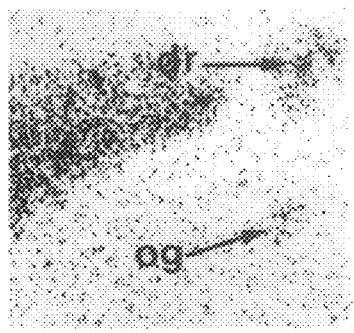

Two lines (13 and 26) had expression in neurons and the third line did not express at all. This shows that the 1163 bp promoter contains regulatory elements sufficient to drive neuron-specific expression in vivo. In the peripheral nervous system PNS, both lines expressed in the same structure. In contrast, in the CNS the labelling pattern of line 26 is a subset of that of line 13. We will only describe line 13 in detail. As expected, most peripheral β2-expressing ganglia expressed β-galactosidase (β-gal), whereas in the CNS only a subset of β2-positive regions expressed the β-gal. For instance, FIG. 4C shows that the vast majority of the neurons of the lumbo-sacral spinal cord express the β2-subunit transcripts, whereas only a subset of neurons in the ventral and dorsal horns display β-gal activity.

Figure 5A:
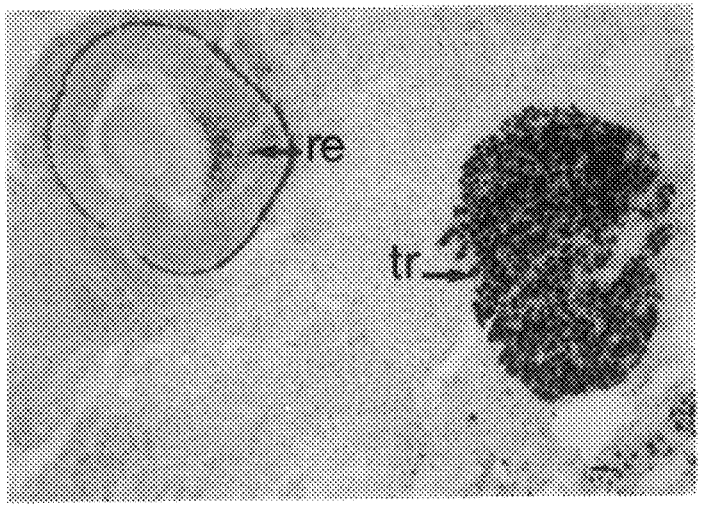
Figure 5C:
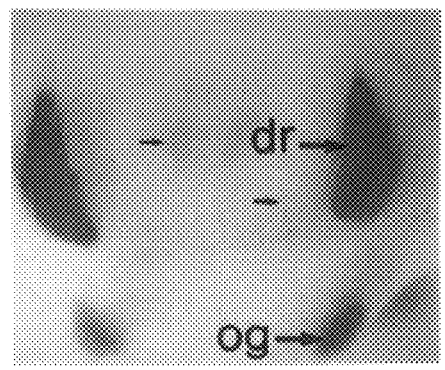
Figure 5B:
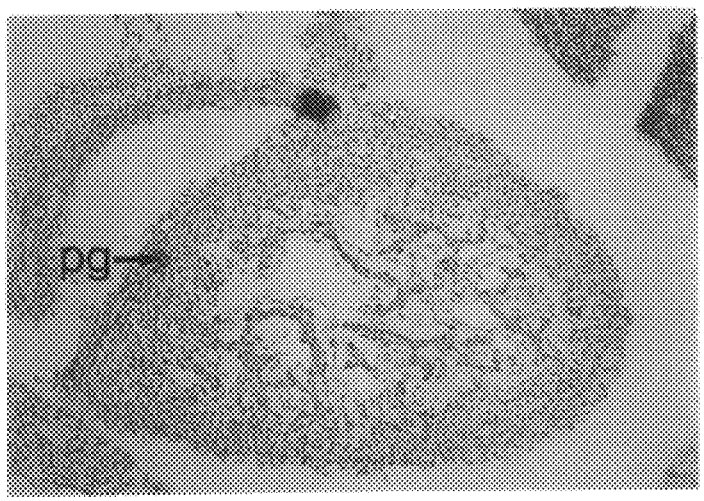
Figure 5D:
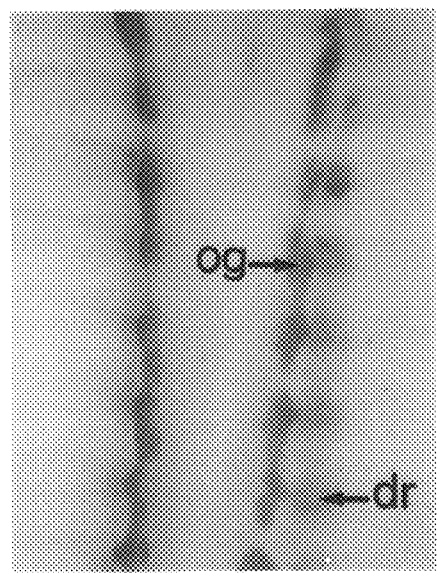

The expression of the transgene could be detected in the peripheral ganglia in E10.5 and E11 embryos. The labelling was examined in E13 total embryos (FIG. 4A) and in brains at later ages (E17, PO and adulthood). At E13, labelling was prominent in PNS: strong labelling was observed in the dorsal root ganglia (DRG, FIGS. 4 and 5 C, D); some ganglia associated with the cranial nerves (the trigeminal see FIG. 5A, geniculate, glossopharyngeal and vagal ganglia); the ganglia of the sympathetic chain (FIG. 5C, D); the ganglionic cells of the retina (FIG. 5A); and putative parasympathetic ganglia in the cardiac wall (FIG. 5B). At E13, clusters of positive cells were also present at several levels of the neuraxis, in both the brainstem and the proencephalon. Clusters of stained neurons were also observed in the ventral and lateral spinal cord.

Later in development (E17), positive neurons were found clustered in several basal telencephalic nuclei whereas dispersed cells were stained in the caudate-putamen. At the diencephalic level, positive clusters were present in the zona incerta and reticular thalamic nucleus, and in many hypothalamic nuclei. In the brainstem, most motor nuclei of cranial nerves (with the exception of the dorsal motor nucleus of the vagus nerve) showed some to high labelling. In addition, the dispersed cells of the V mesencephalic nucleus appeared strongly stained, as well as the pontine nuclei, the prepositus hypoglossal nucleus and a few dispersed cells in the pontine tegmentum.

At PO in line 13, the distribution of positive cells already appeared more restricted than at previous ages (for example labelling in basal telencephalon and oculomotor nuclei was clearly diminished). In the CNS of adult animals labelled cells were detected only in the hypothalamus. In line 13, some clusters of cells were stained in the mucosa of the gastrointestinal tract (stomach and duodenum) and in the pancreas. Ectopic labelling was detected in the genital tubercle and in several superficial muscles of line 13, but none of these tissues were stained in the line 26.

Identification of a Minimal Cell Specific Promoter

To investigate in more detail the regulatory elements involved in the promoter activity, we generated a series of plasmids containing 5' deletions of the 1163 bp promoter. These plasmids were tested by transient transfection into fibroblasts and SK-N-Be cells. These two cell lines were chosen as they were the most easily transfected cell lines. Moreover, the neuroblastoma line was initially isolated from peripheral structures (Biedler et al., 1978) and is a convenient tool to study the regulatory elements carried by the 1163 bp promoter.

When 157 bp were deleted from the 5' end of the 1163 bp promoter (plasmid 1006E-Luci, described in FIG. 1), the luciferase activity did not significantly change in neuroblastomas but increased in fibroblasts (FIG. 6). When 301 bp were further deleted, the activity of the remaining promoter continued to increase in the fibroblasts but not in neuroblastomas (see plasmid 862E-Luci, FIG. 6). Thus, the 157 and 301 bp deleted plasmids carry repressor elements which are only active in fibroblasts. However, the truncated 862 bp promoter still displayed a neuron-specific activity (FIG. 6, compare activity of 862E-Luci in both cell lines), showing that additional regulatory elements are carried by the 1.2 kbp promoter. Moreover, a repressor could be present between −824 and −245 (compare the activities of 862E and 283E-Luci in the neuroblastomas). This putative regulatory element was not further analyzed. Indeed, a 283 bp promoter (plasmid 283E-Luci) is still ≃160 times more active in neuroblastomas than in fibroblasts, confirming the presence of another neuron-specific regulatory elements in this proximal portion of the promoter.

When 150 bp were deleted from the 5' end of the proximal 283 bp promoter, a very strong decrease of the transcriptional activity was detected in both fibroblasts and neuroblastomas (see activity of plasmid 133E-Luci). This shows that crucial positive regulatory elements have been deleted. These positive and negative elements were further investigated by deletion and mutation studies of the proximal portion of the promoter.

Negative and Positive Regulatory Elements in the Proximal Region

The 3' end of the β2-subunit promoter contains putative protein factor binding sites. To analyze the role of these elements in β2-subunit gene regulation, we generated plasmids containing mutations in these binding sites. Using deletion experiments, an activator was detected between −95 and −245 (see FIG. 3, the difference between 283E and 133E-Luci). As the E-box located at nt-118 was a good candidate, we analyzed the effect of mutations in this element on transcriptional activity. Table 1A shows a 40%. reduction of the transcriptional activity of the mutated promoter compared to that of the wild type promoter. The role of the E-box in non-neuronal tissues was more difficult to assess as the basal level of transcription was already low in fibroblasts.

To further understand the role of the E-Box in the regulation of the promoter, we investigated the protein complexes able to interact with this sequence. Gel shift assays were performed using the 33 bp sequence (nt-135 to -103, oligonucleotide E-D) as a probe. When the $^{32}$-P labelled oligonucleotide was mixed with nuclear extracts from neuroblastomas or fibroblasts, three complexes were observed (FIG. 7). All of them were fully displaced by an excess of the unlabelled oligonucleotide E-D. In contrast, no competition was observed when the competitor oligonucleotide was mutated within the E-Box/Dyad (oligonucleotide Mut.E, see FIG. 7 lane "Mut-E"). This shows that the E-box/Dyad is the only element contained within the −135/103 sequence able to bind nuclear protein. This sequence is likely to be involved in the activity of the β-subunit promoter.

An NRSE/RE1 sequence is also present in the proximal region and has been shown to act as a silencer in fibroblasts but not in PC12 cells or neuroblastomas (Kraner et al., 1992; Li et al., 1993; Mori et al., 1992). Point mutation of this sequence in the context of the 1163 bp promoter resulted in a 105-fold increase in the transcriptional activity in fibroblasts, and only a 3-fold increase in neuroblastomas (Table 1A). This sequence is thus responsible for at least part of the cell-specific expression of the β2 subunit gene.

Figure 9A:
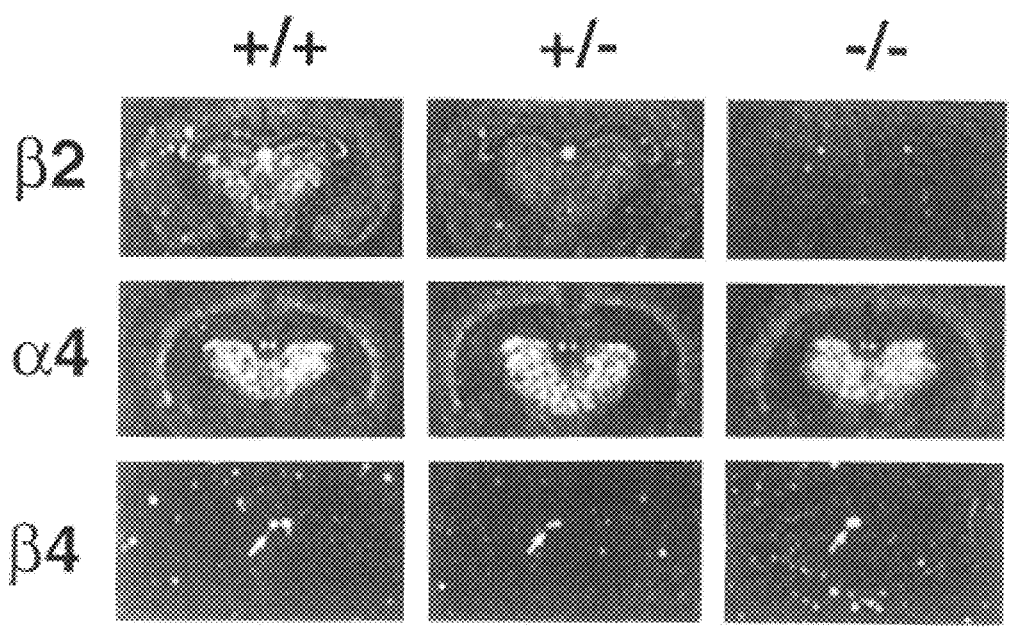

Elimination of High Affinity Nicotine Receptor in Transgenic Mice Results in Alteration of Avoidance Learning The β2-subunit of the nAChR was disrupted in embryonic stem (ES) cells, and mice deficient in this subunit were subsequently generated (FIG. 8). β2-/-mice were viable, mated normally and showed no obvious physical deficits. Overall brain size and organization were normal (see for example FIGS. 9, A and B). Western blot analysis of total brain homogenates using anti-β2 monoclonal 270[11] (FIG. 8d) and immunocytochemistry throughout the brain using a polyclonal anti-β2 antibody[9] demonstrated that the immunoreactivity detected in control mice was absent in β2-/- mice and was diminished in β+/-mice. β2-encoding mRNA was undetectable in β2-/-mice by in situ hybridization using β2-antisense oligonucleotides (FIG. 9A).

The distributions of the α4- and β2-subunits largely overlap in the brain, and these subunits are thought to combine to form the predominant nAChR isoform in the CNS[12]. Based on oocyte expression experiments[6], β4- is the only subunit identified thus far that might also be able to form functional heteropentamers with the α4-subunit. The β4-subunit was expressed normally in the brains of β2+/- mice or β2-/-mice, with expression in the medial habenula (MHb) and the interpeduncular nucleus (IPN)[10], and no upregulation elsewhere in the brain to replace the β2-subunit (FIG. 9A). Nor was the expression of the α4- (FIG. 9A), α5- or β3-subunit mRNAs significantly altered in mutant mice.

Figure 9B:
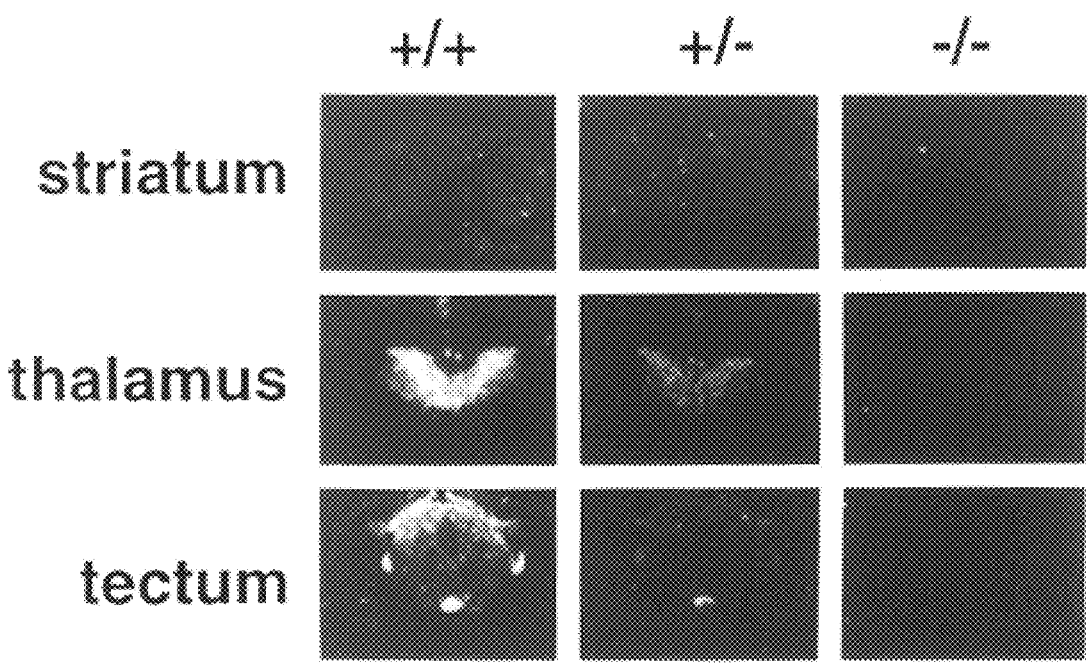

Equilibrium binding experiments have shown that nicotine binds to a population of high affinity sites (KD near 10 nM[13,14]) whose distribution tallies well with that of the α4- and β2-subunits[13-15]. Quantitative receptor autoradiography was performed using $^3$H-nicotine (4 nM) to visualize high affinity nAChR in brain sections from β2 +/+, +/- and -/-mice (FIG. 9B). Nicotine binding in situ was completely abolished in β2-/-animals, and was reduced by approximately 50% in all brain areas in β2+/-animals implicating the β2-subunit in mediating this high affinity binding.

Electrophysiology of Tranogenic Mice

Figure 10A:
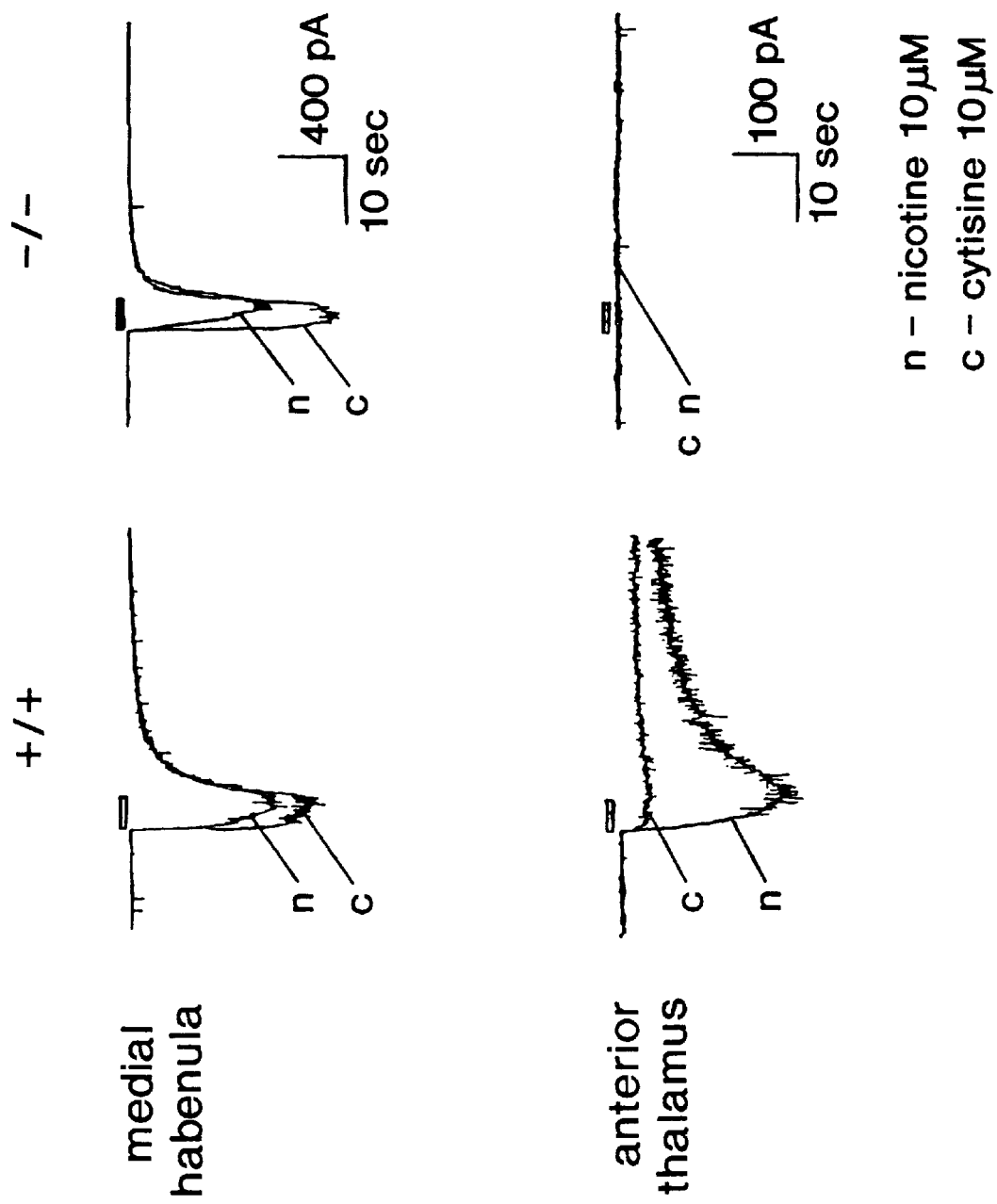

Neurons of the anterior thalamus, which express very high levels of β2 (and α4) subunit mRNAs (FIG. 9A), were studied for an electrophysiological response to nicotine. This area, easily accessible in a slice preparation, responded consistently to 10 μM nicotine in wild type animals with an average inward current of 155+/-73 pA which was blocked by 1 μM dihydro-β-erythroidine. The agonist order of the response was compatible with that seen for α4/β2-containing nicotinic receptors in vitro[6] (nicotine>DMPP>cytisine) (FIG. 10A). Anterior thalamic neurons required several minutes to an hour for complete recovery of the agonist response, suggesting that receptor response is prone to desensitization. Moreover, a relatively high dose of 1 μM was required for a reproducible response, implying that nicotine does not bind to its high affinity site to activate. High affinity nicotine binding sites may therefore be nAChRs in a desensitized conformation.

In β2-/-mice the response of anterior thalamic neurons to nicotine was completely abolished in 100%. of neurons tested (FIG. 10B). As a control, neurons in the MHb, where both α3 and β4 are strongly expressed, were also tested. Nicotine caused an average inward current of 505+/-132 pA in wild type mice, and the agonist potency of this response followed the rank order for the α3/β4 containing receptor (cytisine=nicotine>DMPP) (FIG. 10A). As expected, the response of cells in the MHb to nicotine was maintained in mutant mice.

The β2 subunit is expressed in the ganglia of wild type animals[8-10], but there was no apparent difference in heart rate or basal body temperature. Spontaneous locomotor activity, which is sensitive to high doses of nicotine and is not modified by drugs selective for the β2/α4 isoform of the nAChR[16], was not significantly different in β2-/-, β+/1 and β+/+mice.

Cognitive and Behavioral Results

Learning and memory were examined in mutant and wild type mice using two procedures. The Morris water maze[17,18] evaluates spatial orientation learning. The performance of mutant mice on this test did not differ from that of wild type mice when tested on the visible platform task, or on the hidden platform task (minimum swim-time reached after 5 days of training: mutants (n=8): 7.4+/-1.4 sec; wild type (n=8): 8.2+/-2.0 sec). In the transfer test both groups of animals spent approximately 35% of the time in the platform quadrant, with the same number of platform crossings (mutants: 4+/-0.4; wild type: 3.9+/-0.6).

Retention of an inhibitory avoidance response was assessed using the passive avoidance test, which was also chosen for its pharmacological sensitivity to nicotine administration[19,20]. This test consisted of a training trial in which the mouse was placed in a well-lighted chamber of a shuttle box, and the latency to enter the adjacent dark chamber was measured. Upon entry to the dark chamber, a mild, inescapable foot shock was delivered, and vehicle or nicotine (10 μg/kg) was injected into the mouse. Twenty-four (24) hours later, retention was assessed by measuring the latency to enter the dark chamber. Time spent in the light chamber (retention latency) increased proportionally to the applied foot shock in both mutant and wild type mice. However, treatment with nicotine consistently facilitated retention (p<0.01) by shifting the curve upward by approximately 80 sec only in wild type mice (FIG. 10A). Nicotine administration was completely ineffective in mutant mice. Interestingly, retention latency was significantly higher for mutant mice than for their non-mutant, vehicle-injected siblings (p<0.05) (FIG. 10B).

Increased retention in the passive avoidance test can be observed in animals with a decreased pain threshold or increased emotionality. Therefore, further behavioral testing was performed on all mice included in this experiment. Mutant mice did not differ from their non-mutant siblings for flinch, vocalization or jump response to foot shock. Emotionality was tested by measuring exploratory activity in a two compartment apparatus for 15 min[21,22]. The average time spent in the dark compartment, the locomotor activity in the dark compartment and the transitions between compartments did not differ between the mutant and wild type mice. Therefore, neither changes in pain sensitivity nor changes in emotionality can account for the difference in retention latency observed in passive avoidance testing.

Studies using low doses of nicotine[23] or specific nicotinic agonists[16] suggest that high affinity nAChRs in the brain mediate the effects of nicotine on passive avoidance. Accordingly, nicotine cannot change the performance of β2-/-mice on this test, as they lack high affinity binding sites. The enhanced performance of mutant mice versus wild type mice is quite surprising, however. Several explanations for the paradoxical effect of the β2-subunit mutation can be proposed. One hypothesis is that nicotine injection improves performance of wild type mice on passive avoidance as a result of desensitization, and thus inactivation of nAChRs, leading to enhanced performance on the test. Therefore, the behavior of mice lacking the receptor might mimic that of mice whose receptors have been desensitized[24]. Another possibility is that nAChRs may be present in at least two pathways that interact with opposite effects to generate the behavior measured in passive avoidance. If one pathway is physiologically more active than the other, the inactive pathway will be preferentially stimulated by injection of nicotine in wild type animals, while the more active pathway will be preferentially influenced by β2-gene inactivation.

The experiments described above demonstrate that nAChRs containing the β-subunit mediate the effects of nicotine on passive avoidance, a specific learning task. These mice provide a model system for studying the pharmacological effects of nicotine in the CNS, and are useful in elucidating the role of high affinity nAChRs in cognitive processes, nicotine addiction, and dementias involving deficits of the nicotinic system.

Table 1

Table 1: Positive and negative regulatory elements in the poximal region of the 1163 bp promoter.

In Table 1, Mouse β2 is SEQ ID NO:23, Sodium Channel (nt 29) is SEQ ID NO:24, SCG10 (nt 621) is SEQ ID NO:25, Synapsin I (nt 2070) is SEQ ID NO:26, CAML1 (nt 1535) is SEQ ID NO:27. Calhindin (nt 1093) is SEQ ID NO:28, Neurofilament (nt 383) is SEQ ID NO. 29.

A. Effect of mutations in the proximal part of the 1163 bp promoter. The activities of the wild type or mutated-promoters are normalized to the luciferase activity of the promoterless KS-Luci plasmid. The activities of EE1.2-Luci are from, FIG. 3.

B. Alignment of the proximal silencer of the β-subunit promoter with other neuronal promoters. The sequences are taken from (Maue et al., 1990, Na channel, accession number M31433), (Mori et al., 1990; SCG10, M90489), (Sauerwald et al., 1990;. Synapsin I, M55301), (Kohl et al., 1992; CAML1 gene, X63509), (Gill and Christakos, 1993, Calbindin gene, L11891), (Zopf et al., 1990; Neurofilament gene, X17102, reverse orientation). The numbering refers to the sequences in the GenBank/EMBL library.

TABLE 1

A

|  | Fibroblasts (3T6) |  | Neuroblastomas (SK-N-Be) |  |
|---|---|---|---|---|
| EE1.2-Luci wild type | 1.1 | (100%) | 157 | (100%) |
| EE1.2-Luci/NRSE/RE1 | 115.5 ± 13.8 | (1050%) | 502 ± 204 | (320%) |
| EE1.2-Luci/E-Box | ND |  | 94 ± 14 | (60%) |

B

| Mouse β2 | TGCGCGGC.TTCAGCACCACGGACAGCGC.TCCCGTCC |
|---|---|
| Sodium Channel (nt 29) | ATTGGGTT.TTCAG<u>A</u>ACCACGGACAGC<u>A</u>C.CAGAGTCT |
| SCG10 (nt 621) | AAAGCCAT.TTCAGCACCACGGA<u>G</u>AG<u>T</u>GC.CTCTGCTT |
| Synapsin I (nt 2070) | CTGCCAGC.TTCAGCACCGCGGACAG<u>T</u>GC.CTTCGCCC |
| CAML1 (nt 1535) | TACAGGCC.T<u>C</u>CAGCACCACGGACAGC<u>AG</u>.ACCGTGAA |
| Calbindin (nt 1093) | CCGAACGG.<u>AG</u>CAGCACC<u>G</u>CGGACAGCGC.CCCGCCGC |
| Neurofilament (nt 383) | ATCGGGGT.TTCAGCACCACGGACAGC<u>TC</u>.CCGCGGGG |
|  | TTCAGCACCACGGACAGCGC |

REFERENCES

Each reference below is hereby specifically incorporated into this specification by reference.

Anand, R. and Lindstrom, J. (1990). Nucleotide sequence of the human nicotinic acetylcholine receptor β2 subunit gene. Nucl Acids Res 18, 4272.

Antequera, F. and Bird, A. (1993). Number of CpG islands and genes in human and mouse. Proc Natl Acad Sci U.S.A. 90, 11995–11999.

Ausubel, F., Brent, R., Kingston, R., Moore, D., Seidman, J., Smith, J., and Struhl, K. (1994). Current Protocols in Molecular Biology. (Ed. Janssen, Kareen) John Wisley and Sons, Inc.

Banerjee, S. A., Hoppe, P., Brilliant, M. and Chikaraishi, D. M. (1992). 5' flanking sequences of the rat tyrosine hydroxylase gene target accurate Tissue-Specific, developmental, and transsynaptic expression in transgenic mice. J Neurosci 12, 4460–4467.

Bessereau, J.-L., Mendelzon, D., Le Poupon, C. Fizman, M., Changeux, J.-P. and Piette, J. (1993). Muscle-specific expression of the acetylcholine receptor α-subunit gene requires both positive and negative interactions between myogenic factors, SpI and GBF factors. EMBO J 12,443–449.

Bessereau, J.-L., Stratford-Perricaudet, L., Piette, J., Le Poupon, C. and Changeux, J. P. (1994). In vivo and in vitro analysis of electrical avtivity dependent expression of muscle acetylcholine receptor genes using adenovirus. Proc Natl Acad Sci U.S.A. 91, 1304–1308.

Bessis, A., Savatier, N., Devillers-Thiery, A., Bejanin, S. and Changeux, J. P. (1993). Negative regulatory elements upstream of a novel exon of the neuronal nicotinic acetylcholine receptor alpha-2 subunit gene. *Nucleic Acids Res* 21, 2185–2192.

Biedler, J. L., Roffler-Tarlov, S., Schachner, M. and Freedman, L. (1978). Multiple neurotransmitter synthesis by human neuroblastomas cell lines and clones. *Cancer Res* 38, 3751–3757.

Bourachot, B., Yaniv, M. and Herbomel, P. (1989). Control elements situated downstream of the major transcriptional start site are sufficient for highly efficent polyomavirus late transcription. *J Virol* 63, 2567–2577.

Chen, A., Reyes, A. and Akeson, R. (1990). Transcription initiation sites and structural organization of the extreme 5' region of the rat neural cell adhesion molecule gene. *Mol Cell Biol* 10, 3314–3324.

Daubas, P., Devillers-Thiery, A., Geoffroy, B., Martinez, S., Bessis, A. and Changeux, J. P. (1990). Differential expression of the neuronal acetylcholine receptor α2 subunit gene during chick brain development. *Neuron* 5, 49–60.

Daubas, P., Salmon, A. M., Zoli, M., Geoffroy, B., Devillersthiery, A., Bessis, A., Medevielle, F. and Changeux, J. P. (1993). Chicken Neuronal Acetylcholine Receptor alpha2-Subunit Gene Exhibits Neuron-Specific Expression in the Brain and Spinal Cord of Transgenic Mice. *Proc Natl Acad Sci U.S.A.* 90, 2237–2241.

de Wet, J., Wood, K. V., DeLuca, M., Helinski, D. R. and Subramani, S. (1987). Firefly luciferase gene: Structure and expression in mammalian cells. *Mol Cell Biol* 7, 725–737.

Deneris, E. S., Connolly, J., Boulter, J., Wada, E., Wada, K., Swanson, L. W., Patrick, J. and Heinemann, S. (1988). Primary structure and expression of β2: a novel subunit of neuronal nicotinic acetylcholine receptors. *Neuron* 1, 45–54.

Dong, K W, Yu, K L, and Roberts, J L (1993). Identification of a major up-stream transcription start site for the human progonadotropin-releasing hormone gene used in reproductive tissues and cell lines. *Mol Endocrinol* 7, 1654–1666.

Dumas Milnes Edwards, J.-B., Delort, J. and Mallet, J. (1991). Oligodeoxiribonucleotide ligation to single stranded cDNA: a new tool for cloning 5' ends of mRNAs and for constructing cDNA libraries by in vitro amplification. *Nucl Acids Res* 19, 5227–5232.

Durr, I., Numberger, M., Berberich, C. and Witzemann, V. (1994). Characterization of the functional role of E-box elements for the transcriptional activity of rat acetylcholine receptor ε-subunit and Y-subunit gene promoters in primary muscle cell cultures. *Eur J Biochem* 224, 353–364.

Evrard, C., Borde, I., Marin, P., Galiana, E., Premont, J., Gros, F. and Rouget, P. (1990). Immortalization of bipotential glioneuronal precursor cells. *Proc Natl Acad Sci USA* 87, 3062–3066.

Forss-Petter, S., Danielson, P. E., Catsicas, S., Battenberg, E., Price, J., Nerenberg, M. and Sutcliffe, J. G. (1990). Transgenic mice expressing beta-galactosidase in mature neurons under neuron-specific enolase promoter control. *Neuron* 5, 187–197.

Frohman, M. A., Dush, M. K. and Martin, G. R. (1988). Rapid production of full length cDNA from rare transcripts: amplification using a single gene-specific oligonucleotide primer. *Proc Natl Acad Sci USA* 85, 8998–9002.

Gill, R. K. and Christakos, S. (1993). Identification of sequence elements in mouse calbindin D-28k gene that confer 1,25-dihydroxyvitamin D-3- and butyrate-inducible responses. *Proc Natl Acad Sci. USA* 90, 2984–2988.

Guillemo, F., Lo, L.-C., Johnson, J. E., Auerbach, A., Anderson, D. J. and Joyner, A. L. (1993). Mammalian achaete-scute homolog 1 is required for the early development of olfactory and autonomic neurons. *Cell* 75, 463–476.

Hill, J. A., Zoli, M., Bourgeois, J P. and Changeux, J. P. (1993). Immunocytochemical Localization of a Neuronal Nicotinic Receptor The beta-2-Subunit. *J Neurosci* 13, 1551 –1568.

Hoesche, C., Sauerwald, A., Veh, R. W., Krippl, B. and Kilimann, M. W. (1993). The 5'-Flanking region of the rat Synapsin-I gene directs Neuron-Specific and developmentally regulated reporter gene expression in transgenic mice. *J Biol Chem* 268, 26494–26502.

Hoyle, G. W., Mercer, E. H., Palmiter, R. D. and Brinster, R. L. (1994). Cell-specific expression from the human dopamine beta-hydroxylase promoter in transgenic mice is controlled via a combination of positive and negative regulatory elements. *J Neurosci* 14, 2455–2463.

Kalderon, D., Roberts, B. L., Richardson, W. D. and Smith, A. E. (1984). A short amino acid sequence able to specify nuclear location. *Cell* 39, 499–509.

Kaneda, N., Sasaoka, T., Kobayashi, K., Kiuchi, K., Nagatsu, I., Kurosawa, Y., Fujita, K., Yokoyama, M., Nomura, T., Katsuki, M. and Nagatsu, T. (1991). Tissue-specific and high-level expression of the human tyrosine hydroxylase gene in transgenic mice. *Neuron* 6, 583–594.

Ko, L. J. and Engel, J. D. (1993). DNA-Binding specificities of the GATA transcription factor family. *Mol Cell Biol* 13, 4011–4022.

Kohl, A., Giese, K. P., Mohajeri, M. H., Montag, D., Moos, M. and Schachner, M. (1992). Analysis of promoter activity and 5' genomic structure of neural cell adhesion molecule Li. *J Neurosci Res,* 32, 167–177.

Kraner, S. D., Chong, J. A., Tsay, H.-J. and Mandel, G. (1992). Silencing the Type-II Sodium Channel Gene—A Model for Neural-Specific Gene Regulation. *Neuron* 9, 37–44.

Lamb, N. J. C., Fernandez, A., Tourkine, N., Jeanteur, P. and Blanchard, J.-M. (1990) Demonstration in living cells of intragenic negative regulatory element within the rodent c-fos gene. *Cell* 61, 485–496.

Li, L. A., Suzuki, T., Mori, N. and Greengard, P. (1993). Identification of a Functional Silencer Element Involved in Neuron-Specific Expression of the Synapsin-I Gene. *Proc Natl Acad Sci USA* 90, 1460–1464.

Logan, C., Khoo, W. K., Cado, D. and Joyner, A. L. (1993). 2 Enhancer Regions in the Mouse En-2 Locus Direct Expression to the Mid Hindbrain Region and Mandibular Myoblasts. *Development* 117, 905–916.

Mandel, G. and Mckinnon, D. (1993). Molecular Basis of Neural-Specific Gene Expression. *Annu Rev Neurosci* 16, 323–345.

Matter-Sadzinski, L., Hernandez, M.-C., Roztocil, T., Ballivet, M. and Matter, J.-M. (1992). Neuronal specificity of the α7 nicotinic acetylcholine receptor promoter develops during morphogenesis of the central nervous system. *EMBO J* 11, 4529–4538.

Maue, R., Kraner, S., Goodman, R. and Mandel, G. (1990). Neuron-Specific Expression of the Rat Brain Type II Sodium Channel Gene Is Directed by Upstream Regulatory Elements. *Neuron* 4, 223–231.

Mercer, E., Hoyle, G., Kapur, R., Brinster, R. and Palmiter, R. (1991). The dopamine beta-hydroxylase gene promoter directs expression of *E. coli* lacZ to sympathetic and other neurons in adult transgenic mice. *Neuron* 7, 703–716.

Mori, N., Stein, R., Sigmund, O. and Anderson, D. J. (1990). A Cell Type-Preferred Silencer Element That Controls the Neural-Specific Expression of the SCGIO Gene. *Neuron* 4, 593–594.

Mori, N., Schoenherr, C., Vandenbergh, D. J. and Anderson, D. J. (1992). A Common Silencer Element in the SCG-10 and Type-II Na+ Channel Genes Binds a Factor Present in Nonneuronal Cells But Not in Neuronal Cells. *Neuron* 9, 45–54.

Mulle, C., Vidal, C., Benoit, P. and Changeux, J.-P. (1991). Existence of different subtypes of nicotinic acetylcholine receptors in Rat habenulo-interpeduncuncular. *J Neurosci* 11, 2588–2597.

Nedivi, E., Basi, G., Akey, I. and Skene, J. H. P. (1992). A neural-specific GAP-43 core promoter located between unusual DNA elements that interact to regulate its activity. *J Neurosci* 12, 691–704.

Parker, M. G. (1993). Steroid and related receptors. *Curr Opin Cell Biol* 5, 499–504.

Pioro, E. P. and Cuello, A. C. (1990a). Distribution of nerve growth factor receptor-like immunoreactivity in the adult rat central nervous system. Effect of colchicine and correlation with the cholinergic system-I. Forebrain. *Neuroscience* 34, 57–87.

Pioro, E. P. and Cuello, A. C. (1990b). Distribution of nerve growth factor receptor-like immunoreactivity in the adult rat central nervous system. Effect of colchicine and correlation with the cholinergic system-II. Brainstem, cerebellum and spinal cord. *Neuroscience* 34, 89–110.

Ringstedt, T., Lagercrantz, H. and Persson, H. (1993). Expression of members of the trk family in the developing postnatal rat brain. Dev Brain Res 72, 119–131.

Role, L. W. (1992). Diversity in primary structure and function of neuronal acetylcholine receptor channels. Curr Opin Neurobiol 2, 254–262.

Sassone-Corsi, P. (1988). Cyclic AMP induction of early adenovirus promoters involves sequences required for EIA trans-activation. Proc Natl Acad Sci U.S.A. 85, 7192–7196.

Sauerwald, A., Hoesche, C., Oschwald, R. and Kilimann, M. W. (1990). The 5'-flanking region of the synapsin I gene. A G+C-rich, TATA- and CAAT-less, phylogenetically conserved sequence with cell type-specific promoter function. *J. Biol Chem* 265, 14932–14937

Toussaint, C, Bousquet-Lemercier, B, Garlatti, M, Hanoune, J, and Barouki, R. (1994). Testis-specific transcription start site in the aspartate-aminotransferase housekeeping gene promoter. *J. Biol Chem* 269, 13318–13324

Vanselow, J. Grabczyk, E., Ping, JBaetscher, M., Teng, S. Fishman, M. C. (1994) GAP-43 transgenic mice: dispersed genomic sequences confer a GAP-43-like expression pattern during development and regeneration. *J. Neurosci.* 14,499–510

Wada, E., Wada, K., Boulter, J., Deneris, E., Heinemann, S., Patrick, J. and Swanson, L. W. (1989). Distribution of Alpha2, Alpha3, Alpha4, and Beta2 neuronal nicotinic subunit mRNAs in the central nervous system: a hybridization histochemical study in rat. *J Comp Neurol* 284, 314–335.

Wada, K., Ballivet, M., Boulter, J., Connolly, J., Wada, E., Deneris, E. S., Swanson, L. W., Heinemann, S. and Patrick, J. (1988). Functional expression of a new pharmacological subtype of brain nicotinic acetylcholine receptor. *Science* 240, 330–334.

Yan, Q., and Johnson, E. M. (1988) An immunohistochemical study of the nerve growth factor receptor in developing rats *J. Neurosci* 8, 3481–3498.

Yoon, S. O. and Chikaraishi, D. M. (1994). Isolation of two E-box binding factors that interact with the rat tyrosine hydroxylase enhancer. *J Biol Chem* 269, 18453–18462.

Zoli, M., Le Novere, N., Hill Jr, J. A. and Changeux, J.-P. (1994). Developmental regulation of nicotinic receptor subunit mRNAs in the rat central and peripheral nervous system. *J Neurosci* In press Zopf, D., Dineva, B., Betz, H. and Gundelfinger, E. D. (1990). Isolation of the chicken middle-molecular weight neurofilament (NF-M) gene and characterization of its promoter. *Nucl Ac Res,* 18, 521–529.

Bessis, A., Thesis Dissertation: Regulation de l'expression de genes des sous-unites des recepteurs nicotinique de l'acetylcholine dans le system nerveux., Institute Pasteur, Paris, France, Dec. 14, 1993.

Le Mouellic, H., Brullet, P., WO 90/11354

1 Flicker, C., Dean, R. L., Watkins, D. L., Fisher, S. K. & Bartus, R. T. *Pharm. Biochem. Beh.* 18,973–981 (1983).

2 Levin, E. D. *Psychopharmacology* 108, 417–431 (1992).

3 Sargent, P. B. *Annu. Rev. Neurosci.* 16, 403–443 (1993).

4 Galzi, J.-L., Revah, F:, Bessis, A. & Changeux, J.-P. *Annu. Rev. Phammcol.* 31, 37–72 (1991).

5 Anand, R., Conroy, W. G., Schoepfer, R., Whiting, P. & Lindstrom, J. *J. Biol. Chem* 266, 11192–11198 (1991).

6 Luetje, C. W. & Patrick, J. *J. Neurosci.* 11, 837–845 (1991).

7 Anand, R., Peng, X. & Lindstrom, J. *FEBS Lett.* 327, 241–246 (1993).

8 Wada, E., et al. *J. Comp. Neurol.* 284, 314–335 (1989).

9 Hill, J. A. J., zOli, M., Bourgeois, J.-P. & Changeux, J.-P. *J. Neurosci.* 13, 1551–1568 (1993).

10 Zoli, M., Le Novère, N., Hill, J. A. J. & Changeux, J.-P. *J. Neurosci.* (in press).

11 Swanson, L. W., et al. *Proc. Natl. Acad. Sci. USA* 80, 4532–4536 (1983).

12 Flores, C. M., Rogers, S. W., Pabreza, L. A., Wolfe, B. B. & Kellar, K. J. *Mol. Pharmacol.* 41, 31–37 (1992).

13 Romano, C. & Goldstein, A. *Science* 210, 647–650 (1980).

14 Marks, M. J. & Collins, A. C. *Mol.Pharm.* 22, 554–564 (1982).

15 Marks, M. J., et al. *J. Neurosci.* 12, 2765–2784 (1992).

16 Decker, M., W., et al. *J. Pharmacol. Exp. Ther.* (in press).

17 Morris, R. G. M. *J. Neurosci.* 9, 3040–3057 (1989).

18 Silva, A. J., Paylor, R., Wehner, J. M. & Tonegawa, S. *Science* 257, 206–211 (1992).

19 Faiman, C. P., de Erausquin, G. A. & Baratti, C. M. *Behav. Neural Biol.* 56, 183–199 (1991).

20 Nordberg, A. & Bergh, C. *Acta Pharmacol. Toxicol.* 56, 337–341 (1985).

21 Crawley, J. N. *Neurosci. Biobehav. Rev.* 9, 37–44 (1985).

22 Merlo Pich, E. & Samanin, R. *Pharmacol. Res.* 21, 1–7 (1989).

23 Oliverio, A. J. *Pharm. Exp. Ther.* 154, 350–356 (1966).

24 James, J. R., Villanueva, H. F., Johnson, J. H., Arezo, S. & Rosecrans, J. A. *Psychopharmacology* 114, 456–462 (1994).

25 Le Mouellic, H., Lallernand, Y. & Brulet, P. *Cell* 69, 251–264 (1992).

26 Yagi, T., et al. *Proc. Natl. Acad. Sci. USA* 87, 9918–9922 (1990).

27 Magin, T. M., McWhir, J. & Melton, D. W. *Nucleic Acids Res.* 20, 3795–3796 (1992).

28 Selfridge, J., Pow, A. M., McWhir, J., Magin, T. M. & Melton, D. W. *Somat. Cell Mol. Genet.* 18, 325–336 (1992).

29 Sambrook, J., Fritsch, E. F. & Maniatis, T. *Molecular Cloning; A Laboratory Manual* (Cold Spring Harbor Laboratory Press, Cold Spring Harbor, N.Y., 1989).

30 Clarke, P., Shwartz, R. D., Paul, S. M., Pert, C. B. & Pert, A. *J. Neurosci.* 5, 1307–1313 (1985).

We claim:

1. An isolated DNA selected from the group consisting of:
   (A) the sequence from about nucleotide −1125 to about nucleotide +38 as set forth in FIG. 1 (SEQ ID NO. 22); and
   (B) a sequence having promoter activity, which hybridizes to DNA complementary to said sequence (A) under stringent conditions, wherein said stringent conditions comprise a temperature of about 65° C. and an SSC buffer concentration of about 0.1×SSC.

2. An isolated DNA, comprising the DNA as claimed in claim 1 operatively linked to a nucleotide sequence encoding a polypeptide.

3. An isolated DNA as claimed in claim 2, wherein the polypeptide is encoded by a reporter gene.

4. An isolated DNA as claimed in claim 3, wherein the reporter gene encodes β-galactosidase or Luciferase.

5. An isolated nucleic acid, which hybridizes to the nucleotide sequence (A) of claim 1 under said stringent conditions.

6. An isolated DNA having a sequence comprising the DNA of claim 1 operatively linked to a tumorigenic, oncogenic or immortalizing gene.

7. An isolated DNA, comprising the DNA in claim 1, operatively linked to a heterologous DNA sequence encoding a polypeptide.

8. A recombinant vector containing the nucleotide sequence as claimed in claim 1.

9. A recombinant vector containing the nucleotide sequence of claim 2.

10. An isolated cell, comprising the vector as claimed in claim 9.

11. A cell line, comprising in its genome a foreign nucleotide sequence comprising the DNA as claimed in claim 7.

12. A method of detecting a protein, which binds to a promoter, comprising incubating the DNA as claimed in claim 1 with a nuclear extract under conditions suitable to allow a protein in said nuclear extract to bind to said DNA to form a DNA/protein complex, and detecting said DNA/protein complex.

13. A method as claimed in claim 12 wherein the DNA is the sequence of oligonucleotide E-D, Mut-E, or S-E.

14. A method for isolating a protein, which binds to a promoter, comprising incubating the DNA as claimed in claim 1 with a nuclear extract under conditions suitable to allow a protein in said nuclear extract to bind to said DNA to form a DNA/protein complex, and isolating said protein, which binds to said promoter.

15. An isolated DNA, which is a sequence from about nucleotide −245 to about nucleotide −95 in FIG. 1 (SEQ ID NO. 22).

16. An isolated DNA, consisting of the sequence from about nucleotide −824 to about nucleotide −245 in FIG. 1 (SEQ ID NO. 22).

17. An isolated DNA consisting of the sequence from about nucleotide −135 to about nucleotide −103 in FIG. 1 (SEQ ID NO. 22).

18. An isolated DNA consisting of the sequence from about nucleotide +16 to about nucleotide +36 in FIG. 1 (SEQ ID NO. 22).

19. An isolated DNA selected from the group consisting of the sequence from about nucleotide −968 to about nucleotide +38, the sequence from about nucleotide −824 to about nucleotide +38, and the sequence from about nucleotide −245 to about nucleotide +38, as set forth in FIG. 1 (SEQ ID NO. 22).

20. An isolated DNA selected from the group consisting of:
 (A) the sequence from about nucleotide −1125 to about nucleotide +38 as set forth in FIG. 1 (SEQ ID NO. 22); and
 (B) a sequence having promoter activity, which hybridizes at 65° C. in 0.1×SSC to DNA complementary to said sequence (A).

21. An isolated DNA having the sequence set forth in FIG. 1 (SEQ ID NO. 22).

22. An isolated DNA having a sequence from about nucleotide −1125 to about nucleotide +38 as set forth in FIG. 1 (SEQ ID NO. 22).

23. An isolated DNA, comprising the DNA as claimed in claim 22 operatively linked to a nucleotide sequence encoding a polypeptide.

24. An isolated DNA as claimed in claim 23, wherein the polypeptide is encoded by a reporter gene.

25. An isolated DNA as claimed in claim 24, wherein the reporter gene encodes β-galactosidase or Luciferase.

26. An isolated nucleic acid, comprising a sequence complementary to a nucleotide sequence of claim 22.

27. An isolated DNA having a sequence comprising the DNA of claim 22 operatively linked to a tumorigenic, oncogenic or immortalizing gene.

28. An isolated DNA, comprising the DNA in claim 22, or a fragment of the DNA in claim 22, wherein said fragment has promoter activity and is operatively linked to a heterologous DNA sequence encoding a polypeptide.

29. A recombinant vector containing the nucleotide sequence as claimed in claim 22.

30. A recombinant vector containing the nucleotide sequence of claim 23.

31. An isolated cell, comprising the vector as claimed in claim 30.

32. A cell line comprising in its genome a nucleotide sequence comprising the to the DNA as claimed in claim 28.

33. A method of detecting a protein, which binds to a promoter, comprising incubating the DNA as claimed in claim 22 with a nuclear extract under conditions suitable to allow a protein in said nuclear extract to bind to said DNA to form a DNA/protein complex, and detecting said DNA/protein complex.

34. A method for isolating a protein, which binds to a promoter, comprising incubating the DNA as claimed in claim 22 with a nuclear extract under conditions suitable to allow a protein in said nuclear extract to bind to said DNA to form a DNA/protein complex, and isolating said protein, which binds to said promoter.

35. An isolated DNA having at least one point mutation in a nucleotide sequence from about nucleotide −1125 to about nucleotide +38 as set forth in FIG. 1 (SEQ ID NO. 22), wherein the at least one point mutation is localized between nucleotide −118 and nucleotide −113.

36. An isolated DNA having at least one point mutation in a nucleotide sequence from about nucleotide −1125 to about nucleotide +38 as set forth in FIG. 1 (SEQ ID NO. 22), wherein the at least one point mutation is localized between nucleotide +18 and nucleotide +35.

37. A cloned genomic DNA sequence encoding at least one exon of the mouse β2-subunit of neuronal nicotinic acetylcholine receptor, wherein said exon is selected from the group consisting of exon I, exon II, exon III, and exon IV.

38. A macromolecular complex comprising a DNA as claimed in claim 1 or claim 37 and a protein.

39. Plasmid pSA9, Deposit I-1501 at the Collection Nationale de Cultures de Microorganismes.

40. Plasmid pEAF, Deposit I-1502 at the Collection Nationale de Cultures de Microorganismes.

41. Phage λβ2 nAchR, Deposit I-1503 at the Collection Nationale de Cultures de Microorganismes.

42. An isolated DNA fragment having a regulatory or coding sequence of the mouse β2-subunit of neuronal nicotinic acetylcholine receptor obtainable by cutting the DNA of the phage of claim 41 with restriction enzyme or mechanical shearing.

* * * * *

UNITED STATES PATENT AND TRADEMARK OFFICE
CERTIFICATE OF CORRECTION

PATENT NO. : 6,177,242 B1
DATED : January 23, 2001
INVENTOR(S) : Jean-Pierre Changeux, Marina Picciotto, and Alain Bessis It is certified that error appears in the above-identified patent and that said Letters Patent is hereby corrected as shown below:

Title Page,

Item [75], in the Inventors,
Line 1, after "Changeux", insert -- Paris (FR) --;
Line 2, after "Picciotto", insert -- CT (US) --; and "all of Paris" should read
-- Paris --.

Claim 32, Column 42,
Line 25, after "comprising the", delete "to the".

Signed and Sealed this

Thirty-first Day of July, 2001

Attest:

NICHOLAS P. GODICI
Attesting Officer     Acting Director of the United States Patent and Trademark Office

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

TCGCATGTGG TCCGCAATGA AGCGTACGCC ATCCACTGCT TCCCG                45

(2) INFORMATION FOR SEQ ID NO:2:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

CCTTCTCAAC CTCTGATGTC TTCAAGTCAG GGACCTCAAG GGGGG                45

(2) INFORMATION FOR SEQ ID NO:3:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

ACCAGGCTGA CTTCAAGACC GGGACGCTTC ATGAAGAGGA AGGTG                45

(2) INFORMATION FOR SEQ ID NO:4:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

CTGCATCTAT CTAATGCTCC TCTCGCTACC TGCTCACTCT GCGTGACATC           50

(2) INFORMATION FOR SEQ ID NO:5:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

```
GATGTCACGC AGAGTGAGCA GGTAG                                          25

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGAGTGAGCA GGTAGCGAGA GGAG                                           24

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCAAAGCTGA ACAGCAGCGC CATAG                                          25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGCAGCGCCA TAGAGTTGGA GCACC                                          25

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AGGCGGCTGC GCGGCTTCAG CACCACGGAC                                     30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GCCGCTCCTC TGTGTCAGTA CCCAAAACCC                                     30
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ACATTGGTGG TCATGATCTG                                          20

(2) INFORMATION FOR SEQ ID NO:12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GCGGGATCCG AATTCTTTTT TTTTTTTTTT TTTTTTV                      37

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGAAGTATTC CGCGTACGTG ATG                                      23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

ACCAGGGCGT ATCTCTTCAT AGC                                      23

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

ACCACTTACA                                                                10

(2) INFORMATION FOR SEQ ID NO:16:

(i) SEQUENCE CHARACTERISTICS:
        (A) LENGTH: 10 base pairs (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

ACCACGGACA                                                                      10

(2) INFORMATION FOR SEQ ID NO:17:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

TCCTCAGG                                                                         8

(2) INFORMATION FOR SEQ ID NO:18:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

TCCACTTG                                                                         8

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TCCTCCCCTA GTAGTTCCAC TTGTGTTCCC TAG                                             33

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

CCTCCCCTAG TAGTTCCTCA GGTGTTCCCT AGA                                             33

(2) INFORMATION FOR SEQ ID NO:21:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CTAGCTCCGG GGCGGAGACT CCTCCCCTAG TAGTTCCACT TGTGTTCCCT AG          52
```

(2) INFORMATION FOR SEQ ID NO:22:

(i) SEQUENCE CHARACTERISTICS:
        (A) LENGTH: 1289 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:22:

```
GGAATTCCTG AAAACACTCA AGTTTAAGTA AAAGGTAGGT AGGGGCACTG GGGTGATAAA    60
AGAGCTGGAG GGAACTACAT GTTTAAAAGA CCGAGGGCTA GGAGGGGTTA AATAGTCAAG   120
GATCTTAAAG ACGTCGTCAA TAGCTAGAAT GTGGAGCTGA GACAGGCATT GACGAGATGA   180
AGTCCGAAGC CTTTTGTCTG CTAAGTCTGC TTCAGACAGA AATCTTTTTG GTTGAAAGTG   240
ACCACTGATC CACTAAGAAA AAAAAGAGG TCCTTTTTGG GCTCAGTAGC TAAAACGGCA    300
GGGCTTTCAA GATCAAACAT GTCATTGAGT TTTGACACCT CTCTCATCTT TGCTCTCTTT   360
GTGTTAGCTT CATTCTTTCT GTGAAATGGT CCCCTGATCT CCCCAGAACA CAGCGTGGAA   420
GGAACCATTG ATATTGGTTG CTTATGCAGA TCTCAGAACT TTCAAGGCCA CCTTCTTTTC   480
AGGAGGTCTA GACCTATCTA GCTTAGATTC CCCAGGAGAA TGGCAAGATC TTGGCCTTGT   540
CTGAGCTTAT GGAAGCAGAG AAGGGGGCAG GTGCAAAAGA CTCTCTTCCA GAACTCCGGA   600
GAAATTTGCT TTTCAAAACT AGACAGCACC CTGCTGCCTA CTAAAGAAGT AGGTCCAAGG   660
TCCTAATGTG CATATTCTCC GCTATACTCT TAGCTTTCCA GAAAACTAGA ATCATCAGTT   720
TGGGTAAGAA CATAGAGGAA AACAGAAACG CCCCCCAACC TACCCCATGT CCAGAGAGCC   780
TTGACCTACT TGTCTCCCTC CCACTCTCAA CCCTCCCAGT CTTGCTTCAA ACCTCTCCAC   840
GTCATGCCCC AACTTCGGAG CATTTGAACT CTGAGCAGTG GGGTCGCTTT CGCCTCAAGC   900
ACACCCCACC TCGGCAGGCC CAGTCAAAGG TCCCTCACAG GGACACCTTT TTTTCCCTGG   960
GATCCCGCGC TTCGCCTCCG GGGCGGAGAC TCCTCCCCTA GTAGTTCCAC TTGTGTTCCC  1020
TAGAAGAGCA GCCGGGACGG CAAGAAGCCG GGACCTCCCC CTTCGTTCCA GGAACTGCCG  1080
CGCAGTGGGC ACTTCAGCCC TGGAGGCCGC GAGCCCCACC CGGGTGAAGG CGGCTGCGCG  1140
GCTTCAGCAC CACGGACAGC GCTCCCGTCC GCAGCCCTTG TGTCAGCGAG CGTCCGCGCT  1200
CGCGCTATGC AGGCGCATGG CCCGGTGCTC CAACTCTATG GCGCTGCTGT TCAGCTTTGG  1260
CCTCCTTTGG CTGTGTTCAG GTAAGAATT                                   1289
```

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
TGCGCGGCTT CAGCACCACG GACAGCGCTC CCGTCC                             36
```

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

ATTGGGTTTT CAGAACCACG GACAGCACCA GAGTCT                        36

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

AAAGCCATTT CAGCACCACG GAGAGTGCCT CTGCTT                        36

(2) INFORMATION FOR SEQ ID NO:26:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CTGCCAGCTT CAGCACCGCG GACAGTGCCT TCGCCC                        36

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TACAGGCCTC CAGCACCACG GACAGCAGAC CGTGAA                        36

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CCGAACGGAG CAGCACCGCG GACAGCGCCC CGCCGC                        36

(2) INFORMATION FOR SEQ ID NO:29:

(i) SEQUENCE CHARACTERISTICS:
        (A) LENGTH: 36 base pairs

-continued

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

ATCGGGGTTT CAGCACCACG GACAGCTCCC GCGGGG                         36

(2) INFORMATION FOR SEQ ID NO:30:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GTCGACGGTA CCGCCCGGGC AGGCCTGCTA GCTTAATTAA GCGGCCGCCT CGAGGGGCCC   60

ATGCATGGAT CC                                                      72

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GCCCAGACAT AGGTCACATG ATGGT                                     25

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GTTTATTGCA GCTTATAATG GTTACA                                    26

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

TTCAGCACCA CGGACAGCGC                                           20
```